United States Patent
Austermann et al.

(10) Patent No.: US 11,938,053 B2
(45) Date of Patent: Mar. 26, 2024

(54) FLUID COLLECTION DEVICES, SYSTEMS, AND METHODS

(71) Applicant: PUREWICK CORPORATION, El Cajon, CA (US)

(72) Inventors: Nick Austermann, Atlanta, GA (US); Jason Iain Glithero, McDonough, GA (US); Ashley Marie Johannes, Atlanta, GA (US)

(73) Assignee: PUREWICK CORPORATION

( * ) Notice: Subject to any disclaimer, the term of this patent is extended or adjusted under 35 U.S.C. 154(b) by 499 days.

(21) Appl. No.: 17/051,554

(22) PCT Filed: Apr. 29, 2019

(86) PCT No.: PCT/US2019/029610
§ 371 (c)(1),
(2) Date: Oct. 29, 2020

(87) PCT Pub. No.: WO2019/212951
PCT Pub. Date: Nov. 7, 2019

(65) Prior Publication Data
US 2021/0236323 A1    Aug. 5, 2021

Related U.S. Application Data

(60) Provisional application No. 62/665,321, filed on May 1, 2018.

(51) Int. Cl.
*A61F 5/451* (2006.01)
*A61F 5/44* (2006.01)

(52) U.S. Cl.
CPC ............ *A61F 5/451* (2013.01); *A61F 5/4408* (2013.01)

(58) Field of Classification Search
CPC .............................. A61F 5/451; A61F 5/4408
See application file for complete search history.

(56) References Cited

U.S. PATENT DOCUMENTS

| | | |
|---|---|---|
| 1,032,841 A | 7/1912 | Koenig |
| 1,178,644 A | 4/1916 | Johnson |
| 1,742,080 A | 12/1929 | Jones |
| 1,979,899 A | 11/1934 | Obrien et al. |

(Continued)

FOREIGN PATENT DOCUMENTS

| | | |
|---|---|---|
| AU | 2018216821 A1 | 8/2019 |
| CA | 2165286 C | 9/1999 |

(Continued)

OTHER PUBLICATIONS

US 9,908,683 B2, 03/2018, Sandhausen et al. (withdrawn)

(Continued)

*Primary Examiner* — Guy K Townsend
(74) *Attorney, Agent, or Firm* — Dorsey & Whitney LLP

(57) ABSTRACT

Examples relate to systems, devices, and methods for attaching a fluid collection device to a user or removing fluid collected from a user in the e fluid collection device using a vacuum source operably coupled thereto. The fluid collection devices include urine collection devices shaped to complement the female anatomy near the urethra, attach to the user with one or more flanges, and the vacuum source is operably coupled to the fluid collection device via one or more sections of conduit.

21 Claims, 10 Drawing Sheets

(56) References Cited

U.S. PATENT DOCUMENTS

| | | |
|---|---|---|
| 2,262,772 A | 11/1941 | Peder |
| 2,326,881 A | 8/1943 | Packer |
| 2,379,346 A | 6/1945 | Farrell |
| 2,613,670 A | 10/1952 | Edward |
| 2,616,426 A | 11/1952 | Adele |
| 2,644,234 A | 7/1953 | Earl |
| 2,859,786 A | 11/1958 | Tupper |
| 2,944,551 A | 7/1960 | Carl |
| 2,968,046 A * | 1/1961 | Duke .................. A61G 9/006 604/149 |
| 2,971,512 A | 2/1961 | Reinhardt |
| 3,032,038 A | 5/1962 | Swinn |
| 3,077,883 A | 2/1963 | Hill |
| 3,087,938 A | 4/1963 | Hans et al. |
| 3,194,238 A | 7/1965 | Breece |
| 3,198,994 A | 8/1965 | Hildebrandt et al. |
| 3,221,742 A | 12/1965 | Egon |
| 3,312,981 A | 4/1967 | Mcguire et al. |
| 3,349,768 A | 10/1967 | Keane |
| 3,362,590 A | 1/1968 | Gene |
| 3,366,116 A | 1/1968 | Huck |
| 3,398,848 A | 8/1968 | Donovan |
| 3,400,717 A | 9/1968 | Bruce et al. |
| 3,406,688 A | 10/1968 | Bruce |
| 3,424,163 A * | 1/1969 | Gunnar ............ A61F 13/51121 604/377 |
| 3,425,471 A | 2/1969 | Yates |
| 3,511,241 A | 5/1970 | Lee |
| 3,512,185 A | 5/1970 | Ellis |
| 3,520,300 A | 7/1970 | Flower |
| 3,528,423 A | 9/1970 | Lee |
| 3,613,123 A | 10/1971 | Langstrom |
| 3,648,700 A | 3/1972 | Warner |
| 3,651,810 A | 3/1972 | Ormerod |
| 3,661,155 A | 5/1972 | Lindan |
| 3,699,815 A | 10/1972 | Holbrook |
| 3,726,277 A | 4/1973 | Hirschman |
| 3,742,952 A | 7/1973 | Magers et al. |
| 3,757,355 A | 9/1973 | Allen et al. |
| 3,788,324 A | 1/1974 | Lim |
| 3,843,016 A | 10/1974 | Bornhorst et al. |
| 3,863,638 A | 2/1975 | Rogers et al. |
| 3,863,798 A | 2/1975 | Kurihara et al. |
| 3,864,759 A | 2/1975 | Horiuchi |
| 3,881,486 A | 5/1975 | Fenton |
| 3,915,189 A | 10/1975 | Holbrook et al. |
| 3,998,228 A | 12/1976 | Poidomani |
| 3,999,550 A | 12/1976 | Martin |
| 4,015,604 A | 4/1977 | Csillag |
| 4,020,843 A | 5/1977 | Kanall |
| 4,022,213 A | 5/1977 | Stein |
| 4,027,776 A | 6/1977 | Douglas |
| 4,116,197 A | 9/1978 | Bermingham |
| 4,180,178 A | 12/1979 | Turner |
| 4,187,953 A | 2/1980 | Turner |
| 4,194,508 A | 3/1980 | Anderson |
| 4,200,102 A * | 4/1980 | Duhamel .............. A61F 5/451 604/353 |
| 4,202,058 A | 5/1980 | Anderson |
| 4,233,025 A | 11/1980 | Larson et al. |
| 4,233,978 A | 11/1980 | Hickey |
| 4,246,901 A | 1/1981 | Frosch et al. |
| 4,257,418 A | 3/1981 | Hessner |
| 4,270,539 A | 6/1981 | Frosch et al. |
| 4,281,655 A | 8/1981 | Terauchi |
| 4,292,916 A | 10/1981 | Bradley et al. |
| 4,352,356 A | 10/1982 | Tong |
| 4,360,933 A | 11/1982 | Kimura et al. |
| 4,365,363 A | 12/1982 | Windauer |
| 4,387,726 A | 6/1983 | Denard |
| 4,425,130 A | 1/1984 | Desmarais |
| 4,446,986 A | 5/1984 | Bowen et al. |
| 4,453,938 A | 6/1984 | Brendling |
| 4,457,314 A | 7/1984 | Knowles |
| 4,476,879 A | 10/1984 | Jackson |
| 4,526,688 A | 7/1985 | Schmidt, Jr. et al. |
| 4,528,703 A | 7/1985 | Kraus |
| D280,438 S | 9/1985 | Wendt |
| 4,551,141 A | 11/1985 | Mcneil |
| 4,553,968 A | 11/1985 | Komis |
| 4,581,026 A | 4/1986 | Schneider |
| 4,610,675 A | 9/1986 | Triunfol |
| 4,620,333 A | 11/1986 | Ritter |
| 4,626,250 A | 12/1986 | Schneider |
| 4,627,846 A | 12/1986 | Ternstroem |
| 4,631,061 A | 12/1986 | Martin |
| 4,650,477 A | 3/1987 | Johnson |
| 4,656,675 A | 4/1987 | Fajnsztajn |
| 4,681,570 A | 7/1987 | Dalton |
| 4,692,160 A | 9/1987 | Nussbaumer |
| 4,707,864 A | 11/1987 | Ikematsu et al. |
| 4,713,066 A | 12/1987 | Komis |
| 4,747,166 A * | 5/1988 | Kuntz .................. A61F 5/455 4/144.1 |
| 4,752,944 A | 6/1988 | Conrads et al. |
| 4,769,215 A | 9/1988 | Ehrenkranz |
| 4,772,280 A | 9/1988 | Rooyakkers |
| 4,790,830 A | 12/1988 | Hamacher |
| 4,790,835 A | 12/1988 | Elias |
| 4,791,686 A | 12/1988 | Taniguchi et al. |
| 4,795,449 A * | 1/1989 | Schneider ............ A61F 5/4405 604/326 |
| 4,798,603 A | 1/1989 | Meyer et al. |
| 4,799,928 A | 1/1989 | Crowley |
| 4,804,377 A | 2/1989 | Hanifl et al. |
| 4,812,053 A | 3/1989 | Bhattacharjee |
| 4,820,297 A | 4/1989 | Kaufman et al. |
| 4,846,818 A | 7/1989 | Keldahl et al. |
| 4,846,909 A | 7/1989 | Klug et al. |
| 4,865,595 A | 9/1989 | Heyden |
| 4,880,417 A | 11/1989 | Yabrov et al. |
| 4,882,794 A | 11/1989 | Stewart, III |
| 4,883,465 A | 11/1989 | Brennan |
| 4,886,508 A * | 12/1989 | Washington ............ A61F 5/455 604/347 |
| 4,886,509 A | 12/1989 | Mattsson |
| 4,889,532 A | 12/1989 | Metz et al. |
| 4,889,533 A | 12/1989 | Beecher |
| 4,903,254 A | 2/1990 | Haas |
| 4,905,692 A | 3/1990 | More |
| 4,936,838 A | 6/1990 | Cross et al. |
| 4,955,922 A | 9/1990 | Terauchi |
| 4,957,487 A | 9/1990 | Gerow |
| 4,965,460 A | 10/1990 | Tanaka et al. |
| 4,987,849 A | 1/1991 | Sherman |
| 5,002,541 A | 3/1991 | Conkling et al. |
| 5,004,463 A | 4/1991 | Nigay |
| 5,031,248 A | 7/1991 | Kemper |
| 5,045,077 A | 9/1991 | Blake |
| 5,045,283 A | 9/1991 | Patel |
| 5,049,144 A | 9/1991 | Payton |
| 5,053,339 A | 10/1991 | Patel |
| 5,058,088 A | 10/1991 | Haas et al. |
| 5,071,347 A | 12/1991 | Mcguire |
| 5,078,707 A | 1/1992 | Peter |
| 5,084,037 A | 1/1992 | Barnett |
| 5,100,396 A | 3/1992 | Zamierowski |
| 5,147,301 A | 9/1992 | Ruvio |
| 5,195,997 A | 3/1993 | Carns |
| 5,203,699 A | 4/1993 | Mcguire |
| 5,244,458 A | 9/1993 | Takasu |
| 5,246,454 A | 9/1993 | Peterson |
| 5,267,988 A | 12/1993 | Farkas |
| 5,275,307 A | 1/1994 | Freese |
| 5,294,983 A | 3/1994 | Ersoz et al. |
| 5,295,983 A | 3/1994 | Kubo |
| 5,300,052 A | 4/1994 | Kubo |
| 5,312,383 A | 5/1994 | Kubalak |
| 5,318,550 A | 6/1994 | Cermak et al. |
| 5,340,840 A | 8/1994 | Park et al. |
| 5,382,244 A | 1/1995 | Telang |
| 5,423,784 A | 6/1995 | Metz |
| 5,466,229 A | 11/1995 | Elson et al. |
| 5,478,334 A | 12/1995 | Bernstein |

(56) References Cited

U.S. PATENT DOCUMENTS

| | | |
|---|---|---|
| 5,499,977 A | 3/1996 | Marx |
| 5,543,042 A | 8/1996 | Filan et al. |
| D373,928 S | 9/1996 | Green |
| 5,605,161 A | 2/1997 | Cross |
| 5,618,277 A | 4/1997 | Goulter |
| 5,628,735 A | 5/1997 | Skow |
| 5,636,643 A | 6/1997 | Argenta et al. |
| 5,637,104 A | 6/1997 | Ball et al. |
| 5,674,212 A | 10/1997 | Osborn, III et al. |
| 5,678,564 A | 10/1997 | Lawrence et al. |
| 5,678,654 A | 10/1997 | Uzawa |
| 5,687,429 A | 11/1997 | Rahlff |
| 5,695,485 A | 12/1997 | Duperret et al. |
| 5,752,944 A | 5/1998 | Dann et al. |
| 5,772,644 A | 6/1998 | Bark et al. |
| 5,792,132 A | 8/1998 | Garcia |
| 5,827,243 A | 10/1998 | Palestrant |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,865,378 A | 2/1999 | Hollinshead et al. |
| 5,887,291 A | 3/1999 | Bellizzi |
| 5,894,608 A * | 4/1999 | Birbara .............. A61F 5/4556 604/319 |
| D409,303 S | 5/1999 | Oepping |
| 5,911,222 A | 6/1999 | Lawrence et al. |
| 5,957,904 A | 9/1999 | Holland |
| 5,968,026 A * | 10/1999 | Osborn, III ....... A61F 13/15699 604/378 |
| 5,972,505 A | 10/1999 | Phillips et al. |
| 6,050,983 A | 4/2000 | Moore et al. |
| 6,059,762 A | 5/2000 | Boyer et al. |
| 6,063,064 A | 5/2000 | Tuckey et al. |
| 6,098,625 A | 8/2000 | Winkler |
| 6,105,174 A | 8/2000 | Karlsten et al. |
| 6,113,582 A | 9/2000 | Dwork |
| 6,117,163 A | 9/2000 | Bierman |
| 6,123,398 A * | 9/2000 | Arai .................. B60T 8/17552 303/151 |
| 6,129,718 A | 10/2000 | Wada et al. |
| 6,131,964 A | 10/2000 | Sareshwala |
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,248,096 B1 | 6/2001 | Dwork et al. |
| 6,263,887 B1 | 7/2001 | Dunn |
| 6,311,339 B1 * | 11/2001 | Kraus .................. A61F 5/451 4/144.1 |
| 6,336,919 B1 | 1/2002 | Davis et al. |
| 6,338,729 B1 | 1/2002 | Wada et al. |
| 6,352,525 B1 | 3/2002 | Wakabayashi |
| 6,394,988 B1 | 5/2002 | Hashimoto |
| 6,398,742 B1 | 6/2002 | Kim |
| 6,406,463 B1 | 6/2002 | Brown |
| 6,409,712 B1 | 6/2002 | Dutari et al. |
| 6,416,500 B1 | 7/2002 | Wada et al. |
| 6,428,521 B1 | 8/2002 | Droll |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,540,729 B1 | 4/2003 | Wada et al. |
| 6,547,771 B2 | 4/2003 | Robertson et al. |
| 6,569,133 B2 | 5/2003 | Cheng et al. |
| D476,518 S | 7/2003 | Doppelt |
| 6,592,560 B2 | 7/2003 | Snyder et al. |
| 6,618,868 B2 | 9/2003 | Minnick |
| 6,620,142 B1 | 9/2003 | Flueckiger |
| 6,629,651 B1 | 10/2003 | Male et al. |
| 6,635,038 B2 | 10/2003 | Scovel |
| 6,652,495 B1 | 11/2003 | Walker |
| 6,685,684 B1 | 2/2004 | Falconer |
| 6,702,793 B1 | 3/2004 | Sweetser et al. |
| 6,706,027 B2 * | 3/2004 | Harvie .................. A61F 5/453 604/326 |
| 6,732,384 B2 * | 5/2004 | Scott .................. A47K 11/12 4/144.1 |
| 6,736,977 B1 | 5/2004 | Hall et al. |
| 6,740,066 B2 * | 5/2004 | Wolff .................. A61F 5/451 604/323 |
| 6,764,477 B1 | 7/2004 | Chen et al. |
| 6,783,519 B2 | 8/2004 | Samuelsson |
| 6,796,974 B2 | 9/2004 | Palumbo et al. |
| 6,814,547 B2 | 11/2004 | Childers et al. |
| 6,849,065 B2 | 2/2005 | Schmidt et al. |
| 6,857,137 B2 | 2/2005 | Otto |
| 6,885,690 B2 | 4/2005 | Aggerstam et al. |
| 6,888,044 B2 | 5/2005 | Fell et al. |
| 6,893,425 B2 | 5/2005 | Dunn et al. |
| 6,912,737 B2 | 7/2005 | Ernest et al. |
| 6,918,899 B2 * | 7/2005 | Harvie .................. A61F 5/451 604/326 |
| 6,979,324 B2 | 12/2005 | Bybordi et al. |
| 7,018,366 B2 * | 3/2006 | Easter .................. A61F 5/451 604/327 |
| 7,066,411 B2 | 6/2006 | Male et al. |
| 7,122,023 B1 | 10/2006 | Hinoki |
| 7,125,399 B2 | 10/2006 | Miskie |
| 7,131,964 B2 * | 11/2006 | Harvie .................. A61F 5/455 604/326 |
| 7,135,012 B2 * | 11/2006 | Harvie .................. A61F 5/453 604/326 |
| 7,141,043 B2 * | 11/2006 | Harvie .................. A61F 5/451 604/326 |
| D533,972 S | 12/2006 | La |
| 7,160,273 B2 | 1/2007 | Greter et al. |
| 7,171,699 B2 | 2/2007 | Ernest et al. |
| 7,171,871 B2 | 2/2007 | Kozak |
| 7,179,951 B2 | 2/2007 | Krishnaswamy-mirle et al. |
| 7,181,781 B1 * | 2/2007 | Trabold .................. A61F 5/455 4/144.1 |
| 7,186,245 B1 | 3/2007 | Cheng et al. |
| 7,192,424 B2 | 3/2007 | Cooper |
| 7,220,250 B2 * | 5/2007 | Suzuki .................. A61F 5/451 604/328 |
| D562,975 S | 2/2008 | Otto |
| 7,335,189 B2 * | 2/2008 | Harvie .................. A61F 5/451 604/326 |
| 7,358,282 B2 | 4/2008 | Krueger et al. |
| 7,390,320 B2 * | 6/2008 | Machida .................. A61F 5/455 4/144.1 |
| 7,438,706 B2 | 10/2008 | Koizumi et al. |
| 7,488,310 B2 | 2/2009 | Yang |
| 7,491,194 B1 | 2/2009 | Oliwa |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,585,293 B2 | 9/2009 | Vermaak |
| 7,588,560 B1 | 9/2009 | Dunlop |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 * | 4/2010 | Bengtson .............. A61M 27/00 604/313 |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 * | 7/2010 | Tazoe .................. A61F 5/451 604/320 |
| 7,755,497 B2 * | 7/2010 | Wada .................. A61F 5/451 340/604 |
| 7,766,887 B2 | 8/2010 | Burns, Jr. et al. |
| D625,407 S | 10/2010 | Koizumi et al. |
| 7,806,879 B2 | 10/2010 | Brooks et al. |
| 7,811,272 B2 | 10/2010 | Lindsay et al. |
| 7,815,067 B2 | 10/2010 | Matsumoto et al. |

(56) References Cited

U.S. PATENT DOCUMENTS

| | | | |
|---|---|---|---|
| 7,833,169 B2 | 11/2010 | Hannon | |
| 7,857,806 B2 | 12/2010 | Karpowicz et al. | |
| 7,866,942 B2 | 1/2011 | Harvie | |
| 7,871,385 B2 | 1/2011 | Levinson et al. | |
| 7,875,010 B2 | 1/2011 | Frazier et al. | |
| 7,901,389 B2 | 3/2011 | Mombrinie | |
| 7,927,320 B2 | 4/2011 | Goldwasser et al. | |
| 7,927,321 B2 | 4/2011 | Marland | |
| 7,931,634 B2 | 4/2011 | Swiecicki et al. | |
| 7,939,706 B2 | 5/2011 | Okabe et al. | |
| 7,946,443 B2 | 5/2011 | Stull et al. | |
| 7,947,025 B2 | 5/2011 | Buglino et al. | |
| 7,963,419 B2 | 6/2011 | Burney et al. | |
| 7,976,519 B2 | 7/2011 | Bubb et al. | |
| 7,993,318 B2 | 8/2011 | Olsson et al. | |
| 8,015,627 B2 | 9/2011 | Baker et al. | |
| 8,028,460 B2 | 10/2011 | Williams | |
| 8,047,398 B2 | 11/2011 | Dimartino et al. | |
| 8,083,094 B2 | 12/2011 | Caulfield et al. | |
| 8,128,608 B2 * | 3/2012 | Thevenin | A61F 13/84 604/347 |
| 8,181,651 B2 | 5/2012 | Pinel | |
| 8,181,819 B2 | 5/2012 | Burney et al. | |
| 8,211,063 B2 * | 7/2012 | Bierman | A61M 25/02 604/179 |
| 8,221,369 B2 | 7/2012 | Parks et al. | |
| 8,241,262 B2 | 8/2012 | Mahnensmith | |
| 8,277,426 B2 | 10/2012 | Wilcox et al. | |
| 8,287,508 B1 * | 10/2012 | Sanchez | A61F 5/4404 604/326 |
| 8,303,554 B2 | 11/2012 | Tsai et al. | |
| 8,322,565 B2 | 12/2012 | Caulfield et al. | |
| 8,337,477 B2 | 12/2012 | Parks et al. | |
| D674,241 S | 1/2013 | Bickert et al. | |
| 8,343,122 B2 | 1/2013 | Gorres | |
| 8,353,074 B2 | 1/2013 | Krebs | |
| 8,353,886 B2 | 1/2013 | Bester et al. | |
| D676,241 S | 2/2013 | Merrill | |
| 8,388,588 B2 | 3/2013 | Wada et al. | |
| D679,807 S | 4/2013 | Burgess et al. | |
| 8,425,482 B2 | 4/2013 | Khoubnazar | |
| 8,449,510 B2 | 5/2013 | Martini et al. | |
| D684,260 S | 6/2013 | Lund et al. | |
| 8,470,230 B2 | 6/2013 | Caulfield et al. | |
| 8,479,941 B2 | 7/2013 | Matsumoto et al. | |
| 8,479,949 B2 | 7/2013 | Henkel | |
| 8,512,301 B2 | 8/2013 | Ma | |
| 8,529,530 B2 | 9/2013 | Koch et al. | |
| 8,535,284 B2 | 9/2013 | Joder et al. | |
| 8,546,639 B2 * | 10/2013 | Wada | A61F 5/4401 604/361 |
| 8,551,075 B2 * | 10/2013 | Bengtson | A61M 1/84 604/543 |
| 8,568,376 B2 | 10/2013 | Delattre et al. | |
| D694,404 S | 11/2013 | Burgess et al. | |
| 8,585,683 B2 * | 11/2013 | Bengtson | A61M 1/985 604/543 |
| 8,652,112 B2 | 2/2014 | Johannison et al. | |
| D702,973 S | 4/2014 | Norland et al. | |
| 8,703,032 B2 | 4/2014 | Menon et al. | |
| D704,330 S | 5/2014 | Cicatelli | |
| D704,510 S | 5/2014 | Mason et al. | |
| D705,423 S | 5/2014 | Walsh Cutler | |
| D705,926 S | 5/2014 | Burgess et al. | |
| 8,714,394 B2 | 5/2014 | Wulf | |
| 8,715,267 B2 | 5/2014 | Bengtson et al. | |
| 8,757,425 B2 | 6/2014 | Copeland | |
| 8,777,032 B2 | 7/2014 | Biesecker et al. | |
| 8,808,260 B2 | 8/2014 | Koch et al. | |
| 8,864,730 B2 | 10/2014 | Conway et al. | |
| 8,881,923 B2 | 11/2014 | Higginson | |
| 8,882,731 B2 * | 11/2014 | Suzuki | A61F 5/451 604/327 |
| 8,936,585 B2 | 1/2015 | Carson et al. | |
| D729,581 S | 5/2015 | Boroski | |
| 9,028,460 B2 * | 5/2015 | Medeiros | A61F 5/451 604/347 |
| 9,056,698 B2 | 6/2015 | Noer | |
| 9,078,792 B2 | 7/2015 | Ruiz | |
| 9,173,602 B2 | 11/2015 | Gilbert | |
| 9,173,799 B2 * | 11/2015 | Tanimoto | A61F 5/453 |
| 9,187,220 B2 | 11/2015 | Biesecker et al. | |
| 9,199,772 B2 | 12/2015 | Krippendorf | |
| 9,233,020 B2 | 1/2016 | Matsumiya | |
| 9,248,058 B2 | 2/2016 | Conway et al. | |
| 9,308,118 B1 | 4/2016 | Dupree et al. | |
| 9,309,029 B2 | 4/2016 | Incorvia et al. | |
| 9,333,281 B2 | 5/2016 | Giezendanner et al. | |
| 9,382,047 B2 | 7/2016 | Schmidtner et al. | |
| 9,456,937 B2 | 10/2016 | Ellis | |
| 9,480,595 B2 | 11/2016 | Baham et al. | |
| 9,517,865 B2 | 12/2016 | Albers et al. | |
| D777,941 S | 1/2017 | Piramoon | |
| 9,533,806 B2 | 1/2017 | Ding et al. | |
| 9,550,611 B2 | 1/2017 | Hodge | |
| 9,555,930 B2 | 1/2017 | Campbell et al. | |
| 9,623,159 B2 | 4/2017 | Locke | |
| D789,522 S | 6/2017 | Burgess et al. | |
| 9,687,849 B2 | 6/2017 | Bruno et al. | |
| 9,694,949 B2 | 7/2017 | Hendricks et al. | |
| 9,713,547 B2 | 7/2017 | Lee et al. | |
| 9,788,992 B2 | 10/2017 | Harvie | |
| D804,907 S | 12/2017 | Sandoval | |
| 9,868,564 B2 | 1/2018 | Mcgirr et al. | |
| D814,239 S | 4/2018 | Arora | |
| D817,484 S | 5/2018 | Lafond | |
| 10,037,640 B2 | 7/2018 | Gordon | |
| 10,058,470 B2 | 8/2018 | Phillips | |
| 10,098,990 B2 | 10/2018 | Koch et al. | |
| D835,264 S | 12/2018 | Mozzicato et al. | |
| D835,779 S | 12/2018 | Mozzicato et al. | |
| D840,533 S | 2/2019 | Mozzicato et al. | |
| D840,534 S | 2/2019 | Mozzicato et al. | |
| 10,225,376 B2 | 3/2019 | Perez Martinez | |
| 10,226,376 B2 * | 3/2019 | Sanchez | A61F 5/455 |
| D848,612 S | 5/2019 | Mozzicato et al. | |
| 10,307,305 B1 | 6/2019 | Hodges | |
| 10,335,121 B2 | 7/2019 | Desai | |
| D856,512 S | 8/2019 | Cowart et al. | |
| 10,376,406 B2 * | 8/2019 | Newton | A61F 5/4404 |
| 10,376,407 B2 | 8/2019 | Newton | |
| 10,390,989 B2 * | 8/2019 | Sanchez | A61F 5/453 |
| D858,144 S | 9/2019 | Fu | |
| 10,406,039 B2 | 9/2019 | Villarreal | |
| 10,407,222 B2 | 9/2019 | Allen | |
| 10,478,356 B2 | 11/2019 | Griffin | |
| 10,538,366 B2 | 1/2020 | Pentelovitch et al. | |
| 10,569,938 B2 | 2/2020 | Zhao et al. | |
| 10,577,156 B2 | 3/2020 | Dagnelie et al. | |
| 10,618,721 B2 | 4/2020 | Vazin | |
| D884,390 S | 5/2020 | Wang | |
| 10,669,079 B2 | 6/2020 | Freedman et al. | |
| D892,315 S | 8/2020 | Airy | |
| 10,730,672 B2 | 8/2020 | Bertram et al. | |
| 10,737,848 B2 | 8/2020 | Philip et al. | |
| 10,765,854 B2 | 9/2020 | Law et al. | |
| 10,766,670 B2 | 9/2020 | Kittmann | |
| 10,799,386 B1 | 10/2020 | Harrison | |
| D901,214 S | 11/2020 | Hu | |
| 10,857,025 B2 * | 12/2020 | Davis | A61F 5/455 |
| 10,865,017 B1 | 12/2020 | Cowart et al. | |
| 10,889,412 B2 | 1/2021 | West et al. | |
| 10,913,581 B2 | 2/2021 | Stahlecker | |
| D912,244 S | 3/2021 | Rehm et al. | |
| 10,952,889 B2 * | 3/2021 | Newton | A61F 5/4404 |
| 10,973,678 B2 * | 4/2021 | Newton | A61M 1/71 |
| 10,974,874 B2 | 4/2021 | Ragias et al. | |
| 11,000,401 B2 | 5/2021 | Ecklund et al. | |
| D923,365 S | 6/2021 | Wang | |
| 11,026,829 B2 * | 6/2021 | Harvie | A61M 25/0017 |
| 11,027,900 B2 | 6/2021 | Liu | |
| 11,045,346 B2 | 6/2021 | Argent et al. | |
| D928,946 S * | 8/2021 | Sanchez | D24/122 |

(56) References Cited

U.S. PATENT DOCUMENTS

| | | |
|---|---|---|
| 11,179,506 B2 | 11/2021 | Barr et al. |
| 11,226,376 B2 | 1/2022 | Yamauchi et al. |
| 11,376,152 B2 * | 7/2022 | Sanchez ............... A61F 5/455 |
| 11,382,786 B2 * | 7/2022 | Sanchez ............... A61F 5/4404 |
| 11,382,788 B2 | 7/2022 | Hjorth et al. |
| 11,426,303 B2 * | 8/2022 | Davis .................. A61F 5/455 |
| 11,529,252 B2 * | 12/2022 | Glithero ............... A61F 5/453 |
| 2001/0037097 A1 | 11/2001 | Cheng et al. |
| 2001/0054426 A1 | 12/2001 | Knudson et al. |
| 2002/0019614 A1 * | 2/2002 | Woon ................ A61F 13/53747 |
| | | 604/378 |
| 2002/0026161 A1 | 2/2002 | Grundke |
| 2002/0087131 A1 | 7/2002 | Wolff et al. |
| 2002/0091364 A1 | 7/2002 | Prabhakar |
| 2002/0189992 A1 | 12/2002 | Schmidt et al. |
| 2002/0193760 A1 | 12/2002 | Thompson |
| 2003/0004436 A1 | 1/2003 | Schmidt et al. |
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1 | 10/2003 | Harvie |
| 2003/0233079 A1 | 12/2003 | Parks et al. |
| 2004/0006321 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 * | 7/2004 | Easter ................ A61F 5/451 |
| | | 604/322 |
| 2004/0147894 A1 | 7/2004 | Mizutani et al. |
| 2004/0158221 A1 | 8/2004 | Mizutani et al. |
| 2004/0176731 A1 | 9/2004 | Cheng et al. |
| 2004/0191919 A1 | 9/2004 | Unger et al. |
| 2004/0207530 A1 * | 10/2004 | Nielsen ................ A61F 13/42 |
| | | 340/573.5 |
| 2004/0236292 A1 * | 11/2004 | Tazoe ................ A61F 5/451 |
| | | 604/317 |
| 2004/0254547 A1 * | 12/2004 | Okabe ................ A61F 5/455 |
| | | 604/317 |
| 2005/0010182 A1 | 1/2005 | Parks et al. |
| 2005/0033248 A1 * | 2/2005 | Machida ............... A61F 5/455 |
| | | 604/327 |
| 2005/0065471 A1 | 3/2005 | Kuntz |
| 2005/0070861 A1 * | 3/2005 | Okabe ................ A61F 5/4404 |
| | | 604/327 |
| 2005/0070862 A1 * | 3/2005 | Tazoe ................ A61F 5/455 |
| | | 604/327 |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0273920 A1 | 12/2005 | Marinas |
| 2005/0277904 A1 | 12/2005 | Chase et al. |
| 2005/0279359 A1 | 12/2005 | LeBlanc et al. |
| 2006/0004332 A1 | 1/2006 | Marx |
| 2006/0015080 A1 | 1/2006 | Mahnensmith |
| 2006/0015081 A1 * | 1/2006 | Suzuki ................ A61F 5/451 |
| | | 604/329 |
| 2006/0016778 A1 | 1/2006 | Park |
| 2006/0079854 A1 | 4/2006 | Kay et al. |
| 2006/0111648 A1 * | 5/2006 | Vermaak ............... A61B 10/007 |
| | | 604/355 |
| 2006/0155214 A1 * | 7/2006 | Wightman ............. A61F 5/455 |
| | | 600/574 |
| 2006/0200102 A1 | 9/2006 | Cooper |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0277670 A1 | 12/2006 | Baker et al. |
| 2007/0006368 A1 | 1/2007 | Key et al. |
| 2007/0038194 A1 * | 2/2007 | Wada .................. A61F 5/451 |
| | | 604/347 |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0135786 A1 | 6/2007 | Schmidt et al. |
| 2007/0149935 A1 | 6/2007 | Dirico |
| 2007/0191804 A1 | 8/2007 | Coley |
| 2007/0214553 A1 * | 9/2007 | Carromba ............. A47K 11/12 |
| | | 4/144.4 |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 * | 2/2008 | Okabe ................ A61F 5/4404 |
| | | 604/378 |
| 2008/0041869 A1 | 2/2008 | Backaert |
| 2008/0091153 A1 * | 4/2008 | Harvie ................ A61F 5/451 |
| | | 604/318 |
| 2008/0091158 A1 | 4/2008 | Yang |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0281282 A1 | 11/2008 | Finger et al. |
| 2008/0287894 A1 * | 11/2008 | Van Den Heuvel .... A61F 5/455 |
| | | 604/327 |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0192482 A1 * | 7/2009 | Dodge, II ......... A61F 13/53708 |
| | | 524/436 |
| 2009/0234312 A1 | 9/2009 | Otoole et al. |
| 2009/0251510 A1 | 10/2009 | Noro et al. |
| 2009/0264840 A1 | 10/2009 | Virginio |
| 2009/0270822 A1 * | 10/2009 | Medeiros ............... A61F 5/451 |
| | | 604/347 |
| 2009/0281510 A1 | 11/2009 | Fisher |
| 2010/0004612 A1 * | 1/2010 | Thevenin ............... A61F 13/84 |
| | | 4/443 |
| 2010/0058660 A1 | 3/2010 | Williams |
| 2010/0121289 A1 | 5/2010 | Parks et al. |
| 2010/0185168 A1 * | 7/2010 | Graauw ................ A61F 5/4556 |
| | | 604/347 |
| 2010/0198172 A1 | 8/2010 | Wada et al. |
| 2010/0211032 A1 * | 8/2010 | Tsai .................. A61F 5/453 |
| | | 604/319 |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 * | 2/2011 | Wada ................ A61F 5/4401 |
| | | 604/318 |
| 2011/0040271 A1 * | 2/2011 | Rogers ................ A61F 5/4556 |
| | | 604/346 |
| 2011/0054426 A1 | 3/2011 | Stewart et al. |
| 2011/0060300 A1 * | 3/2011 | Weig ................ A61F 5/451 |
| | | 604/319 |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 * | 7/2011 | Wada .................. A61F 13/42 |
| | | 604/385.01 |
| 2011/0202024 A1 | 8/2011 | Cozzens |
| 2011/0238023 A1 | 9/2011 | Slayton |
| 2011/0240648 A1 | 10/2011 | Tucker |

(56) References Cited

U.S. PATENT DOCUMENTS

| | | |
|---|---|---|
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1* | 5/2012 | Wheaton .............. A61F 5/453 128/885 |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0210503 A1* | 8/2012 | Anzivino, Sr. ....... A61F 5/4556 4/144.3 |
| 2012/0233761 A1 | 9/2012 | Huang |
| 2012/0245541 A1* | 9/2012 | Suzuki .................. A61F 13/42 604/319 |
| 2012/0245542 A1* | 9/2012 | Suzuki .................. A61F 13/84 374/45 |
| 2012/0245547 A1 | 9/2012 | Wilcox et al. |
| 2012/0253303 A1* | 10/2012 | Suzuki .................. A61F 13/42 374/45 |
| 2012/0271259 A1 | 10/2012 | Ulert |
| 2012/0296305 A1 | 11/2012 | Barraza Khaled et al. |
| 2012/0330256 A1 | 12/2012 | Wilcox et al. |
| 2013/0006206 A1* | 1/2013 | Wada .................. A61F 13/535 604/385.01 |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0245496 A1 | 9/2013 | Wells et al. |
| 2013/0245586 A1 | 9/2013 | Jha |
| 2013/0292537 A1 | 11/2013 | Dirico |
| 2014/0031774 A1* | 1/2014 | Bengtson ............... A61M 1/90 604/319 |
| 2014/0157499 A1 | 6/2014 | Suzuki et al. |
| 2014/0171889 A1 | 6/2014 | Hopman et al. |
| 2014/0182051 A1* | 7/2014 | Tanimoto ............... A61G 9/006 4/144.3 |
| 2014/0196189 A1 | 7/2014 | Lee et al. |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0359660 A1* | 12/2015 | Harvie ................... A61F 5/441 604/351 |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1* | 4/2016 | Timm .................... A61F 13/84 604/385.01 |
| 2016/0113809 A1 | 4/2016 | Kim |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1* | 12/2016 | Newton ............... A01K 23/005 |
| 2016/0367411 A1 | 12/2016 | Justiz et al. |
| 2016/0374848 A1* | 12/2016 | Sanchez ................ A61F 5/453 604/319 |
| 2017/0007438 A1* | 1/2017 | Harvie .................. A61F 5/453 |
| 2017/0014560 A1 | 1/2017 | Minskoff et al. |
| 2017/0100276 A1 | 4/2017 | Joh |
| 2017/0128638 A1 | 5/2017 | Giezendanner et al. |
| 2017/0143534 A1 | 5/2017 | Sanchez |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1* | 9/2017 | Sanchez ............... A61F 5/4404 |
| 2017/0266658 A1 | 9/2017 | Bruno et al. |
| 2017/0281399 A1* | 10/2017 | VanMiddendorp ..... A61F 5/455 |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0042748 A1 | 12/2017 | Griffin |
| 2017/0348139 A1* | 12/2017 | Newton ............... A61F 5/4404 |
| 2017/0354532 A1 | 12/2017 | Holt |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0028349 A1* | 2/2018 | Newton ................. A61M 1/71 |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1* | 8/2018 | Davis .................... A61F 5/451 |
| 2018/0256384 A1 | 9/2018 | Kasirye |
| 2018/0271694 A1 | 9/2018 | Fernandez et al. |
| 2018/0317892 A1 | 11/2018 | Catlin |
| 2019/0001030 A1 | 1/2019 | Braga et al. |
| 2019/0021899 A1 | 1/2019 | Vlet |
| 2019/0038451 A1* | 2/2019 | Harvie .................. A61F 5/441 |
| 2019/0046102 A1 | 2/2019 | Kushnir et al. |
| 2019/0100362 A1 | 4/2019 | Meyers et al. |
| 2019/0133814 A1 | 5/2019 | Tammen et al. |
| 2019/0142624 A1* | 5/2019 | Sanchez ................ A61F 5/453 604/319 |
| 2019/0224036 A1* | 7/2019 | Sanchez ................ A61F 5/443 |
| 2019/0247222 A1 | 8/2019 | Ecklund et al. |
| 2019/0247223 A1 | 8/2019 | Brun et al. |
| 2019/0282391 A1 | 9/2019 | Johannes et al. |
| 2019/0314189 A1 | 10/2019 | Acosta |
| 2019/0314190 A1* | 10/2019 | Sanchez ............... A61F 5/453 |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2020/0008985 A1 | 1/2020 | Nguyen et al. |
| 2020/0030595 A1 | 1/2020 | Boukidjian et al. |
| 2020/0046544 A1* | 2/2020 | Godinez ............... A61F 5/451 |
| 2020/0055638 A1 | 2/2020 | Lau et al. |
| 2020/0070392 A1 | 3/2020 | Huber et al. |
| 2020/0085610 A1 | 3/2020 | Cohn et al. |
| 2020/0086090 A1 | 3/2020 | Von Weymarn-schärli et al. |
| 2020/0129322 A1 | 4/2020 | Leuckel |
| 2020/0171217 A9 | 6/2020 | Braga et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315838 A1 | 10/2020 | Eckert |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |

(56) References Cited

U.S. PATENT DOCUMENTS

| | | | |
|---|---|---|---|
| 2020/0375781 A1 | 12/2020 | Staali et al. | |
| 2020/0385179 A1 | 12/2020 | Mccourt | |
| 2020/0390591 A1* | 12/2020 | Glithero | A61F 5/455 |
| 2020/0390592 A1 | 12/2020 | Merrill | |
| 2020/0405521 A1 | 12/2020 | Glasroe | |
| 2021/0008771 A1 | 1/2021 | Huber et al. | |
| 2021/0009323 A1 | 1/2021 | Markarian et al. | |
| 2021/0059853 A1* | 3/2021 | Davis | A61F 5/451 |
| 2021/0061523 A1 | 3/2021 | Bytheway | |
| 2021/0069005 A1* | 3/2021 | Sanchez | A61F 5/4404 |
| 2021/0069008 A1 | 3/2021 | Blabas et al. | |
| 2021/0077993 A1 | 3/2021 | Nazareth et al. | |
| 2021/0113749 A1 | 4/2021 | Radl et al. | |
| 2021/0121318 A1 | 4/2021 | Pinlac | |
| 2021/0137724 A1 | 5/2021 | Ecklund et al. | |
| 2021/0154055 A1 | 5/2021 | Villarreal | |
| 2021/0170079 A1 | 6/2021 | Radl et al. | |
| 2021/0220162 A1 | 7/2021 | Jamison | |
| 2021/0220163 A1 | 7/2021 | Mayrand | |
| 2021/0228400 A1 | 7/2021 | Glithero | |
| 2021/0228401 A1 | 7/2021 | Becker et al. | |
| 2021/0228795 A1* | 7/2021 | Hughett | A61F 5/455 |
| 2021/0229877 A1 | 7/2021 | Ragias et al. | |
| 2021/0236323 A1* | 8/2021 | Austermann | A61F 5/451 |
| 2021/0267787 A1 | 9/2021 | Nazemi | |
| 2021/0275343 A1* | 9/2021 | Sanchez | A61F 5/4404 |
| 2021/0315727 A1 | 10/2021 | Jiang | |
| 2021/0353450 A1 | 11/2021 | Sharma et al. | |
| 2021/0361469 A1 | 11/2021 | Liu et al. | |
| 2021/0369495 A1* | 12/2021 | Cheng | A61F 5/4405 |
| 2021/0386925 A1 | 12/2021 | Hartwell et al. | |
| 2021/0393433 A1 | 12/2021 | Godinez et al. | |
| 2022/0023091 A1 | 1/2022 | Ecklund et al. | |
| 2022/0047410 A1 | 2/2022 | Walthall | |
| 2022/0062027 A1 | 3/2022 | Mitchell et al. | |
| 2022/0062029 A1* | 3/2022 | Johannes | A61F 5/4401 |
| 2022/0066825 A1 | 3/2022 | Saraf et al. | |
| 2022/0071811 A1* | 3/2022 | Cheng | A61F 5/453 |
| 2022/0071826 A1 | 3/2022 | Kulkarni et al. | |
| 2022/0104965 A1 | 4/2022 | Vaninetti et al. | |
| 2022/0104981 A1 | 4/2022 | Jones | |
| 2022/0117774 A1* | 4/2022 | Meyer | A61F 5/455 |
| 2022/0117775 A1* | 4/2022 | Jones | A61L 26/0009 |
| 2022/0133524 A1* | 5/2022 | Davis | A61M 1/80 604/319 |
| 2022/0151817 A1* | 5/2022 | Mann | A61F 5/451 |
| 2022/0218510 A1 | 7/2022 | Metzger et al. | |
| 2022/0229053 A1 | 7/2022 | Levin et al. | |
| 2022/0248836 A1 | 8/2022 | Cagle et al. | |
| 2022/0257407 A1* | 8/2022 | Johannes | A61F 5/455 |
| 2022/0265462 A1* | 8/2022 | Alder | A61F 5/455 |
| 2022/0273482 A1 | 9/2022 | Johannes et al. | |
| 2022/0280357 A1* | 9/2022 | Jagannathan | A61F 13/84 |
| 2022/0313474 A1 | 10/2022 | Kriscovich et al. | |
| 2022/0354685 A1* | 11/2022 | Davis | A61B 5/208 |
| 2022/0370231 A1 | 11/2022 | Wang et al. | |
| 2022/0370234 A1 | 11/2022 | Hughett et al. | |
| 2022/0370237 A1 | 11/2022 | Parmar et al. | |
| 2022/0387001 A1 | 12/2022 | Askenazi et al. | |
| 2022/0395391 A1 | 12/2022 | Saunders et al. | |
| 2023/0018845 A1 | 1/2023 | Lee | |
| 2023/0020563 A1 | 1/2023 | Sharma et al. | |
| 2023/0037159 A1 | 2/2023 | Brennan et al. | |
| 2023/0062994 A1 | 3/2023 | Ecklund et al. | |
| 2023/0089032 A1 | 3/2023 | Hughett et al. | |
| 2023/0105001 A1 | 4/2023 | Whittome et al. | |
| 2023/0138269 A1 | 5/2023 | Abdelal et al. | |
| 2023/0145365 A1 | 5/2023 | Martin et al. | |
| 2023/0277362 A1* | 9/2023 | Davis | A61B 5/208 604/319 |

FOREIGN PATENT DOCUMENTS

| | | |
|---|---|---|
| CA | 2354132 A1 | 6/2000 |
| CA | 2488867 C | 8/2007 |
| CA | 3050918 A1 | 8/2018 |
| CA | 3098571 A1 | 11/2019 |
| CN | 2269203 Y | 12/1997 |
| CN | 1332620 A | 1/2002 |
| CN | 1533755 A | 10/2004 |
| CN | 1602825 A | 4/2005 |
| CN | 1720888 A | 1/2006 |
| CN | 2006026108 A | 2/2006 |
| CN | 2936204 Y | 8/2007 |
| CN | 101262836 A | 9/2008 |
| CN | 102159159 A | 8/2011 |
| CN | 202184840 U | 4/2012 |
| CN | 102481441 A | 5/2012 |
| CN | 103533968 A | 1/2014 |
| CN | 103717180 A | 4/2014 |
| CN | 204562697 U | 8/2015 |
| CN | 105451693 A | 3/2016 |
| CN | 205849719 U | 1/2017 |
| CN | 107847384 A | 3/2018 |
| CN | 107920912 A | 4/2018 |
| CN | 209285902 U | 8/2019 |
| CN | 211198839 U | 8/2020 |
| CN | 114375187 A | 4/2022 |
| CN | 116096332 A | 5/2023 |
| DE | 1516466 A1 | 6/1969 |
| DE | 2721330 A1 | 11/1977 |
| DE | 2742298 A1 | 3/1978 |
| DE | 9407554.9 U1 | 5/1995 |
| DE | 4443710 A1 | 6/1995 |
| DE | 19619597 A1 | 11/1997 |
| DE | 102011103783 A1 | 12/2012 |
| DE | 202015104597 U1 | 7/2016 |
| DK | 9600118 | 11/1996 |
| EP | 0032138 A2 | 7/1981 |
| EP | 0066070 B1 | 12/1982 |
| EP | 0274753 A2 | 7/1988 |
| EP | 0119143 B1 | 11/1988 |
| EP | 0610638 A1 | 8/1994 |
| EP | 0613355 A1 | 9/1994 |
| EP | 0613355 B1 | 1/1997 |
| EP | 0966936 A1 | 12/1999 |
| EP | 0987293 A1 | 3/2000 |
| EP | 1063953 A1 | 1/2001 |
| EP | 0653928 B1 | 10/2002 |
| EP | 1332738 A1 | 8/2003 |
| EP | 1382318 A1 | 1/2004 |
| EP | 1089684 B1 | 10/2004 |
| EP | 1616542 A1 | 1/2006 |
| EP | 1382318 B1 | 5/2006 |
| EP | 1063953 B1 | 1/2007 |
| EP | 1872752 A1 | 1/2008 |
| EP | 2180907 A1 | 5/2010 |
| EP | 2380532 A1 | 10/2011 |
| EP | 2389908 A1 | 11/2011 |
| EP | 2601916 A1 | 6/2013 |
| EP | 2676643 A1 | 12/2013 |
| EP | 2997950 A2 | 3/2016 |
| EP | 2879534 B1 | 3/2017 |
| EP | 3424471 A1 | 1/2019 |
| EP | 3169292 B1 | 11/2019 |
| EP | 3788992 A1 | 3/2021 |
| EP | 3576689 B1 | 3/2022 |
| EP | 3752110 B1 | 3/2022 |
| EP | 4025163 A1 | 7/2022 |
| GB | 1011517 A | 12/1965 |
| GB | 1467144 A | 3/1977 |
| GB | 2106395 A | 4/1983 |
| GB | 2106784 A | 4/1983 |
| GB | 2148126 A | 5/1985 |
| GB | 2171315 A | 8/1986 |
| GB | 2148126 B | 7/1987 |
| GB | 2191095 A | 12/1987 |
| GB | 2199750 A | 7/1988 |
| GB | 2260907 A | 5/1993 |
| GB | 2462267 A | 2/2010 |

(56) References Cited

FOREIGN PATENT DOCUMENTS

| | | |
|---|---|---|
| GB | 2469496 A | 10/2010 |
| GB | 2490327 A | 10/2012 |
| GB | 2507318 A | 4/2014 |
| IT | 201800009129 A1 | 4/2020 |
| JP | S5410596 A | 1/1979 |
| JP | S5410596 Y2 | 5/1979 |
| JP | S55155618 A | 12/1980 |
| JP | S5888596 U | 6/1983 |
| JP | S63107780 U | 7/1988 |
| JP | H0267530 A | 3/1990 |
| JP | H02103871 A | 4/1990 |
| JP | H02131422 A | 5/1990 |
| JP | H0460220 A | 2/1992 |
| JP | H05123349 A | 5/1993 |
| JP | H05123350 A | 5/1993 |
| JP | H085630 A | 1/1996 |
| JP | H1040141 A | 2/1998 |
| JP | H10225430 A | 8/1998 |
| JP | H11113946 A | 4/1999 |
| JP | H11290365 A | 10/1999 |
| JP | 2000116690 A | 4/2000 |
| JP | 2000185068 A1 | 7/2000 |
| JP | 3087938 B2 | 9/2000 |
| JP | 2001054531 A | 2/2001 |
| JP | 2001070331 A | 3/2001 |
| JP | 2001276107 A | 10/2001 |
| JP | 2001276108 A | 10/2001 |
| JP | 2002028173 A | 1/2002 |
| JP | 2003505152 A | 2/2003 |
| JP | 2003180722 A | 7/2003 |
| JP | 2004130056 A | 4/2004 |
| JP | 2004267530 A | 9/2004 |
| JP | 2005066011 A | 3/2005 |
| JP | 2005066325 A | 3/2005 |
| JP | 2005518237 A | 6/2005 |
| JP | 3749097 B2 | 12/2005 |
| JP | 3123547 B2 | 6/2006 |
| JP | 2006136492 A | 6/2006 |
| JP | 2006204868 A | 8/2006 |
| JP | 2007044494 A | 2/2007 |
| JP | 3132659 B2 | 5/2007 |
| JP | 4039641 B2 | 11/2007 |
| JP | 2009509570 A | 3/2009 |
| JP | 2009101738 A1 | 8/2009 |
| JP | 2010081981 A | 4/2010 |
| JP | 4640772 B2 | 12/2010 |
| JP | 2010536439 A | 12/2010 |
| JP | 4747166 B2 | 5/2011 |
| JP | 2011087823 A | 5/2011 |
| JP | 4801218 B1 | 8/2011 |
| JP | 2011218130 A | 11/2011 |
| JP | 2011224070 A | 11/2011 |
| JP | 2012523869 A | 10/2012 |
| JP | 2013238608 A | 11/2013 |
| JP | 2014521960 A | 8/2014 |
| JP | 2015092945 A | 5/2015 |
| JP | 3198994 B2 | 7/2015 |
| JP | 2019525811 A | 9/2019 |
| JP | 2021120686 A | 8/2021 |
| KR | 200290061 Y1 | 9/2002 |
| KR | 20030047451 A | 6/2003 |
| KR | 20140039485 A | 4/2014 |
| KR | 101432639 B1 | 8/2014 |
| KR | 20180106659 A | 10/2018 |
| KR | 20180108774 A | 10/2018 |
| PT | 2068717 E | 6/2013 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009007702 A4 | 7/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 201 1024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013082397 A1 | 6/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016124203 A1 | 8/2016 |

(56) References Cited

FOREIGN PATENT DOCUMENTS

| | | |
|---|---|---|
| WO | 2016139448 A1 | 9/2016 |
| WO | 2016166562 A1 | 10/2016 |
| WO | 2016167535 A1 | 10/2016 |
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017075226 A1 | 5/2017 |
| WO | 2017152198 A1 | 9/2017 |
| WO | 2017153357 A1 | 9/2017 |
| WO | 2017162559 A1 | 9/2017 |
| WO | 2017205446 A1 | 11/2017 |
| WO | 2017209779 A1 | 12/2017 |
| WO | 2017210524 A1 | 12/2017 |
| WO | 2018022414 A1 | 2/2018 |
| WO | 2018044781 A1 | 3/2018 |
| WO | 2018056953 A1 | 3/2018 |
| WO | 2018090550 A1 | 5/2018 |
| WO | 2018138513 A1 | 8/2018 |
| WO | 2018144318 A1 | 8/2018 |
| WO | 2018144463 A1 | 8/2018 |
| WO | 2018150263 A1 | 8/2018 |
| WO | 2018150268 A1 | 8/2018 |
| WO | 2018152156 A1 | 8/2018 |
| WO | 2018183791 A1 | 10/2018 |
| WO | 2018150267 A3 | 11/2018 |
| WO | 2018235026 A1 | 12/2018 |
| WO | 2018235065 A1 | 12/2018 |
| WO | 2019004404 A1 | 1/2019 |
| WO | 2019065541 A1 | 4/2019 |
| WO | 2019096845 A1 | 5/2019 |
| WO | 2019150385 A1 | 8/2019 |
| WO | 2019161094 A1 | 8/2019 |
| WO | 2019188566 A1 | 10/2019 |
| WO | 2019190593 A1 | 10/2019 |
| WO | 2019212949 A1 | 11/2019 |
| WO | 2019212950 A1 | 11/2019 |
| WO | 2019212951 A1 | 11/2019 |
| WO | 2019212952 A1 | 11/2019 |
| WO | 2019212954 A1 | 11/2019 |
| WO | 2019212955 A1 | 11/2019 |
| WO | 2019212956 A1 | 11/2019 |
| WO | 2019214787 A1 | 11/2019 |
| WO | 2019214788 A1 | 11/2019 |
| WO | 2020000994 A1 | 1/2020 |
| WO | 2020020618 A1 | 1/2020 |
| WO | 2020038822 A1 | 2/2020 |
| WO | 2020088409 A1 | 5/2020 |
| WO | 2020049394 A3 | 6/2020 |
| WO | 2020120657 A1 | 6/2020 |
| WO | 2020152575 A1 | 7/2020 |
| WO | 2020182923 A1 | 9/2020 |
| WO | 2020204967 A1 | 10/2020 |
| WO | 2020209898 A1 | 10/2020 |
| WO | 2020242790 A1 | 12/2020 |
| WO | 2020251893 A1 | 12/2020 |
| WO | 2020256865 A1 | 12/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016300 A1 | 1/2021 |
| WO | 2021025919 A1 | 2/2021 |
| WO | 2021034886 A1 | 2/2021 |
| WO | 2021041123 A1 | 3/2021 |
| WO | 2021086868 A1 | 5/2021 |
| WO | 2021094352 A1 | 5/2021 |
| WO | 2021102296 A1 | 5/2021 |
| WO | 2021138411 A1 | 7/2021 |
| WO | 2021138414 A1 | 7/2021 |
| WO | 2021155206 A1 | 8/2021 |
| WO | 2021173436 A1 | 9/2021 |
| WO | 2021195384 A1 | 9/2021 |
| WO | 2021207621 A1 | 10/2021 |
| WO | 2021211568 A1 | 10/2021 |
| WO | 2021216419 A1 | 10/2021 |
| WO | 2021216422 A1 | 10/2021 |
| WO | 2021247523 A1 | 12/2021 |
| WO | 2021257202 A1 | 12/2021 |
| WO | 2022006256 A1 | 1/2022 |
| WO | 2022031943 A1 | 2/2022 |
| WO | 2022035745 A1 | 2/2022 |
| WO | 2022076427 A2 | 4/2022 |
| WO | 2022086898 A1 | 4/2022 |
| WO | 2022098536 A1 | 5/2022 |
| WO | 2022125685 A1 | 6/2022 |
| WO | 2022140545 A1 | 6/2022 |
| WO | 2022150360 A1 | 7/2022 |
| WO | 2022150463 A1 | 7/2022 |
| WO | 2022159392 A1 | 7/2022 |
| WO | 2022170182 A1 | 8/2022 |
| WO | 2022182385 A1 | 9/2022 |
| WO | 2022192188 A1 | 9/2022 |
| WO | 2022192347 A1 | 9/2022 |
| WO | 2023014641 A1 | 2/2023 |
| WO | 2023038945 A1 | 3/2023 |
| WO | 2023038950 A1 | 3/2023 |
| WO | 2023049175 A1 | 3/2023 |

OTHER PUBLICATIONS

Advisory Action for U.S. Appl. No. 16/905,400 dated Jun. 9, 2021.
Final Office Action for U.S. Appl. No. 16/899,956 dated Apr. 19, 2021.
Final Office Action for U.S. Appl. No. 16/905,400 dated Apr. 6, 2021.
Final Office Action for U.S. Appl. No. 17/088,272 dated May 25, 2021.
Notice of Allowance for U.S. Appl. No. 14/952,591 dated Apr. 5, 2021.
Notice of Allowance for U.S. Appl. No. 29/624,661 dated Apr. 28, 2021.
Notice of Allowance for U.S. Appl. No. 29/694,002 dated Apr. 29, 2021.
Restriction Requirement for U.S. Appl. No. 16/478,180 dated May 25, 2021.
U.S. Appl. No. 17/330,657 dated May 26, 2021
Boehringer CareDry System—Second Generation for Non-Invasive Urinary Management for Females, Mar. 2021, 3 pgs.
Advisory Action for U.S. Appl. No. 14/722,613 dated Mar. 4, 2019.
Advisory Action for U.S. Appl. No. 14/952,591 dated Jun. 1, 2018.
Advisory Action for U.S. Appl. No. 15/238,427 dated Apr. 10, 2019.
Corrected International Search Report and Written Opinion for International Application No. PCT/US2017/043025 dated Jan. 11, 2018.
Corrected Notice of Allowability for U.S. Appl. No. 15/221,106 dated Jul. 2, 2019.
Final Office Action for U.S. Appl. No. 14/722,613 dated Nov. 29, 2018.
Final Office Action for U.S. Appl. No. 14/947,759 dated Apr. 8, 2016.
Final Office Action for U.S. Appl. No. 14/952,591 dated Feb. 23, 2018.
Final Office Action for U.S. Appl. No. 14/952,591 dated Nov. 1, 2019.
Final Office Action for U.S. Appl. No. 14/952,591 dated Nov. 27, 2020.
Final Office Action for U.S. Appl. No. 15/171,968 dated Feb. 14, 2020.
Final Office Action for U.S. Appl. No. 15/171,968 dated Mar. 19, 2019.
Final Office Action for U.S. Appl. No. 15/221,106 dated Jan. 23, 2019.
Final Office Action for U.S. Appl. No. 15/238,427 dated Jan. 2, 2019.
Final Office Action for U.S. Appl. No. 15/260,103 dated Feb. 14, 2019.
Final Office Action for U.S. Appl. No. 15/612,325 dated Sep. 17, 2020.

(56) References Cited

OTHER PUBLICATIONS

Final Office Action for U.S. Appl. No. 29/624,661 dated Feb. 18, 2020.
International Search Report and Written Opinion from International Application No. PCT/US2016/049274 dated Dec. 1, 2016.
International Search Report and Written Opinion from International Application No. PCT/US2017/035625 dated Aug. 15, 2017.
International Search Report and Written Opinion from International Application No. PCT/US2017/043025 dated Oct. 18, 2017.
International Search Report and Written Opinion from International Application No. PCT/US2018/015968 dated Apr. 6, 2018.
International Search Report and Written Opinion from International Application No. PCT/US2019/029608 dated Sep. 3, 2019.
International Search Report and Written Opinion from International Application No. PCT/US2019/029609 dated Sep. 3, 2019.
International Search Report and Written Opinion from International Application No. PCT/US2019/029610 dated Sep. 3, 2019.
International Search Report and Written Opinion from International Application No. PCT/US2019/029611 dated Jul. 3, 2019.
International Search Report and Written Opinion from International Application No. PCT/US2019/029613 dated Jul. 3, 2019.
International Search Report and Written Opinion from International Application No. PCT/US2019/029614 dated Sep. 26, 2019.
International Search Report and Written Opinion from International Application No. PCT/US2019/029616 dated Aug. 30, 2019.
International Search Report and Written Opinion from International Application No. PCT/US2020/023572 dated Jul. 6, 2020.
Issue Notification for U.S. Appl. No. 15/221,106 dated Jul. 24, 2019.
Issue Notification for U.S. Appl. No. 15/238,427 dated Jul. 24, 2019.
Issue Notification for U.S. Appl. No. 15/260,103 dated Aug. 7, 2019.
Issue Notification for U.S. Appl. No. 15/611,587 dated Feb. 20, 2019.
Non-Final Office Action for U.S. Appl. No. 14/722,613 dated Jun. 13, 2019.
Non-Final Office Action for U.S. Appl. No. 14/947,759, dated Mar. 17, 2016.
Non-Final Office Action for U.S. Appl. No. 14/952,591 dated Aug. 1, 2017.
Non-Final Office Action for U.S. Appl. No. 14/952,591 dated Mar. 20, 2020.
Non-Final Office Action for U.S. Appl. No. 14/952,591 dated Mar. 21, 2019.
Non-Final Office Action for U.S. Appl. No. 14/952,591 dated Sep. 28, 2018.
Non-Final Office Action for U.S. Appl. No. 15/171,968 dated May 11, 2020.
Non-Final Office Action for U.S. Appl. No. 15/171,968 dated Aug. 20, 2019.
Non-Final Office Action for U.S. Appl. No. 15/171,968 dated Jun. 12, 2018.
Non-Final Office Action for U.S. Appl. No. 15/221,106 dated Jun. 5, 2018.
Non-Final Office Action for U.S. Appl. No. 15/238,427 dated Aug. 8, 2018.
Non-Final Office Action for U.S. Appl. No. 15/260,103 dated Sep. 26, 2018.
Non-Final Office Action for U.S. Appl. No. 15/611,587 dated Dec. 29, 2017.
Non-Final Office Action for U.S. Appl. No. 15/611,587 dated Jul. 13, 2018.
Non-Final Office Action for U.S. Appl. No. 15/612,325 dated Mar. 19, 2020.
Non-Final Office Action for U.S. Appl. No. 16/899,956 dated Oct. 16, 2020.
Non-Final Office Action for U.S. Appl. No. 16/904,868 dated Nov. 25, 2020.
Non-Final Office Action for U.S. Appl. No. 16/905,400 dated Dec. 2, 2020.
Non-Final Office Action for U.S. Appl. No. 29/624,661 dated Jul. 18, 2019.
Non-Final Office Action for U.S. Appl. No. 29/694,002 dated Jun. 24, 2020.
Notice of Allowance for U.S. Appl. No. 15/171,968 dated Nov. 6, 2020.
Notice of Allowance for U.S. Appl. No. 15/221,106 dated May 1, 2019.
Notice of Allowance for U.S. Appl. No. 15/238,427 dated May 23, 2019.
Notice of Allowance for U.S. Appl. No. 15/260,103 dated Jun. 7, 2019.
Notice of Allowance for U.S. Appl. No. 15/611,587 dated Dec. 21, 2018.
Notice of Allowance for U.S. Appl. No. 15/612,325 dated Jan. 21, 2021.
Notice of Allowance for U.S. Appl. No. 29/624,661 dated Jul. 10, 2020.
Notice of Allowance for U.S. Appl. No. 29/624,661 dated May 14, 2020.
Notice of Allowance for U.S. Appl. No. 29/624,661 dated Sep. 29, 2020.
Notice of Allowance for U.S. Appl. No. 29/694,002 dated Oct. 16, 2020.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/611,587, filed Jun. 1, 2017.
U.S. Appl. No. 15/612,325, filed Jun. 2, 2017.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 29/741,751, filed Jul. 15, 2020.
U.S. Appl. No. 62/452,437, filed Jan. 31, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,889, filed May 29, 2019.
U.S. Appl. No. 62/873,045, filed Jul. 11, 2019.
U.S. Appl. No. 62/873,048, filed Jul. 11, 2019.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126 filed Aug. 11, 2020.
U.S. Appl. No. 63/071,438, filed Aug. 28, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.

(56) References Cited

OTHER PUBLICATIONS

U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/094,464, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
Defendant and Counterclaim Plaintiff Sage Products, LLC's Answer, Defenses, and Counterclaims to Plaintiff's Amended Complaint, Nov. 1, 2019.
Sage's Initial Invalidity Contentions Regarding U.S. Pat. Nos. 8,287,508; 10,226,375; and 10,390,989, May 29, 2020, 193 pages.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Sage's Second Supplemental Invalidity Contentions Regarding U.S. Pat. Nos. 8,287,508, 10,226,375, 10,390,989, and 10,376,407, 292 pages.
Excerpts from the 508 (U.S. Pat. No. 8,278,508) Patent's Prosecution History, 2020, 99 pages.
Plaintiff's Opening Claim Construction Brief, Case No. 19-1508-MN, Oct. 16, 2020, 26 pages.
Plaintiff's Identification of Claim Terms and Proposed Constructions, Case No. 19-1508-MN, 3 pages.
PureWick's Response to Interrogatory No. 9 in *PureWick, LLC* v. *Sage Products, LLC*, Case No. 19-1508-MN, Mar. 23, 2020, 6 pages.
Sage's Preliminary Identification of Claim Elements and Proposed Constructions for U.S. Pat. Nos. 8,287,508, 10,226,376, 10,390,989 and 10,376,407, Case No. 19-1508-MN, 7 pages.
Corrected Certificate of Service, Case No. IPR2020-01426, U.S. Pat. No. 8,287,508, 2020, 2 pages.
Declaration of Diane K. Newman Curriculum Vitae, Petition for Interparties Review, 2020, pp. 1-199.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, Omni Medical, 8 pages.
"AMXDmax In-Flight Bladder Relief", Omni Medical; Omni Medical Systems, Inc., 2015.
"AMXDX—Advanced Mission Extender Device Brochure", Omni Medical, Omni Brochure—http://www.omnimedicalsys.com/uploads/AMXDFixedWing.pdf, 2 pages.
"How Period Panties Work", www.shethinx.com/pages/thinx-itworks, 2020, 10 pages.
"In Flight Bladder Relief", Omni Medical, Omni Presentation https://www.omnimedicalsys.com/uploads/AMXDmax_HSD.pdf, 14 pages.
"Research and Development Work Relating to Assistive Technology Jun. 2005", British Department of Health, Nov. 2006, 40 pages.
"Step by Step How Ur24 WorksHome", http://medicalpatentur24.com, last accessed Dec. 6, 2017, Aug. 30, 2017, 4 pages.
"Underwear that absorbs your period", Thinx!, https://www.shethinx.com/pages/thinx-it-works last accessed Jun. 24, 2020, 7 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, MD&DI, 2014, 4 pages.
Hollister, Female Urinary and Pouch and Male Urinary Pouch Brochure, 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.
Hollister, "Retracted Penis Pouch by Hollister", Vitality Medical.com, https://www.vitalitymedical.com/hollister-retracted-penis-pouch.html last accessed Jun. 24, 2020, 6 pages.
Macaulay, et al., "A Noninvasive Continence Management System: Development and Evaluation of a Novel Toileting Device for Women", The Wound, Ostomy and Continence Nurses Society, vol. 34 No. 6, 2007, pp. 641-648.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Parmar, "10 Finalists Chosen for Dare-to-Dream Medtech Design Challenge (PureWick)", Design Services, Nov. 10, 2014, 3 pages.
Purewick, "Incontinence Relief for Women", Presentation, Sep. 23, 2015, 7 pages.
Pytlik, "Super Absorbent Polymers", University of Buffalo, http://www.courses.sens.buffalo.edu/ce435/Diapers/Diapers.html, accessed on Feb. 17, 2017.
Sachtman, "New Relief for Pilots? It Depends", Wired, https://www.wired.com/2008/05/pilot-relief/, 2008, 2 pages.
Corrected Notice of Allowability for U.S. Appl. No. 15/612,325 dated Mar. 17, 2021.
Final Office Action for U.S. Appl. No. 16/904,868 dated Mar. 26, 2021.
Issue Notification for U.S. Appl. No. 15/171,968 dated Mar. 3, 2021.
Issue Notification for U.S. Appl. No. 15/612,325 dated Mar. 24, 2021.
Notice of Allowance for U.S. Appl. No. 15/171,968 dated Feb. 16, 2021.
Notice of Allowance for U.S. Appl. No. 15/612,325 dated Feb. 19, 2021.
Notice of Allowance for U.S. Appl. No. 29/694,002 dated Jan. 29, 2021.
Notice to File Missing Parts for U.S. Appl. No. 17/179,116 dated Mar. 3, 2021.
U.S. Appl. No. 17/179,116, filed Feb. 18, 2021.
Memorandum Order, Feb. 2021, 14 pgs.
Decision Granting Institution of Inter Partes Review for U.S. Pat. No. 8,287,508, Case No. 2020-01426, Feb. 17, 2021, 39 pages.
Advisory Action for U.S. Appl. No. 16/245,726 dated Apr. 19, 2023.
Advisory Action for U.S. Appl. No. 16/369,676 dated Mar. 24, 2023.
Advisory Action for U.S. Appl. No. 16/433,773 dated Feb. 15, 2023.
Advisory Action for U.S. Appl. No. 16/452,258 dated Oct. 26, 2022.
Advisory Action for U.S. Appl. No. 16/478,180 dated Sep. 21, 2022.
Advisory Action for U.S. Appl. No. 16/478,180 dated Sep. 7, 2023.
Advisory Action for U.S. Appl. No. 16/899,956 dated Jul. 9, 2021.
Advisory Action for U.S. Appl. No. 16/904,868 dated Jul. 2, 2021.
Advisory Action for U.S. Appl. No. 16/904,868 dated Jun. 15, 2022.
Advisory Action for U.S. Appl. No. 16/905,400 dated Feb. 16, 2022.
Advisory Action for U.S. Appl. No. 17/051,550 dated Sep. 8, 2023.
Advisory Action for U.S. Appl. No. 17/444,792 dated Aug. 25, 2023.
Advisory Action for U.S. Appl. No. 17/662,700 dated Jan. 30, 2023.
Corrected Notice of Allowability for U.S. Appl. No. 17/330,657 dated Dec. 9, 2021.
Final Office Action for U.S. Appl. No. 16/245,726 dated Nov. 25, 2022.
Final Office Action for U.S. Appl. No. 16/369,676 dated Aug. 31, 2023.
Final Office Action for U.S. Appl. No. 16/369,676 dated Dec. 5, 2022.
Final Office Action for U.S. Appl. No. 16/433,773 dated Oct. 25, 2022.
Final Office Action for U.S. Appl. No. 16/449,039 dated Aug. 1, 2022.
Final Office Action for U.S. Appl. No. 16/452,145 dated Mar. 25, 2022.
Final Office Action for U.S. Appl. No. 16/452,258 dated Jun. 14, 2022.
Final Office Action for U.S. Appl. No. 16/478,180 dated Jun. 22, 2022.

(56) References Cited

OTHER PUBLICATIONS

Final Office Action for U.S. Appl. No. 16/478,180 dated May 31, 2023.
Final Office Action for U.S. Appl. No. 16/904,868 dated Mar. 10, 2022.
Final Office Action for U.S. Appl. No. 16/905,400 dated Dec. 9, 2021.
Final Office Action for U.S. Appl. No. 17/051,399 dated Mar. 9, 2023.
Final Office Action for U.S. Appl. No. 17/051,550 dated May 23, 2023.
Final Office Action for U.S. Appl. No. 17/051,585 dated Jul. 27, 2023.
Final Office Action for U.S. Appl. No. 17/444,792 dated Jun. 15, 2023.
Final Office Action for U.S. Appl. No. 17/446,256 dated Sep. 19, 2023.
Final Office Action for U.S. Appl. No. 17/448,811 dated Aug. 3, 2023.
Final Office Action for U.S. Appl. No. 17/451,345 dated May 3, 2023.
Final Office Action for U.S. Appl. No. 17/653,137 dated Sep. 21, 2023.
Final Office Action for U.S. Appl. No. 17/655,464 dated Sep. 1, 2023.
Final Office Action for U.S. Appl. No. 17/662,700 dated Sep. 30, 2022.
International Search Report and Written Opinion from International Application No. PCT/IB2021/057173 dated Nov. 5, 2021.
International Search Report and Written Opinion from International Application No. PCT/US2020/033064 dated Aug. 31, 2020.
International Search Report and Written Opinion from International Application No. PCT/US2020/033122 dated Aug. 31, 2020.
International Search Report and Written Opinion from International Application No. PCT/US2020/040860 dated Oct. 2, 2020.
International Search Report and Written Opinion from International Application No. PCT/US2020/041242 dated Nov. 17, 2020.
International Search Report and Written Opinion from International Application No. PCT/US2020/041249 dated Oct. 2, 2020.
International Search Report and Written Opinion from International Application No. PCT/US2020/042262 dated Oct. 14, 2020.
International Search Report and Written Opinion from International Application No. PCT/US2020/043059 dated Oct. 6, 2020.
International Search Report and Written Opinion from International Application No. PCT/US2020/044024 dated Nov. 12, 2020.
International Search Report and Written Opinion from International Application No. PCT/US2020/046914 dated Dec. 1, 2020.
International Search Report and Written Opinion from International Application No. PCT/US2020/055680 dated Dec. 15, 2020.
International Search Report and Written Opinion from International Application No. PCT/US2020/057562 dated Jan. 27, 2021.
International Search Report and Written Opinion from International Application No. PCT/US2020/061563 dated Feb. 19, 2021.
International Search Report and Written Opinion from International Application No. PCT/US2020/065234 dated Apr. 12, 2021.
International Search Report and Written Opinion from International Application No. PCT/US2020/067451 dated Mar. 25, 2021.
International Search Report and Written Opinion from International Application No. PCT/US2020/067454 dated Mar. 29, 2021.
International Search Report and Written Opinion from International Application No. PCT/US2020/067455 dated Mar. 26, 2021.
International Search Report and Written Opinion from International Application No. PCT/US2021/015024 dated May 18, 2021.
International Search Report and Written Opinion from International Application No. PCT/US2021/015787 dated May 27, 2021.
International Search Report and Written Opinion from International Application No. PCT/US2021/023001 dated Jun. 21, 2021.
International Search Report and Written Opinion from International Application No. PCT/US2021/024162 dated Jul. 8, 2021.
International Search Report and Written Opinion from International Application No. PCT/US2021/026607 dated Jul. 29, 2021.
International Search Report and Written Opinion from International Application No. PCT/US2021/027061 dated Jul. 19, 2021.
International Search Report and Written Opinion from International Application No. PCT/US2021/027104 dated Jul. 6, 2021.
International Search Report and Written Opinion from International Application No. PCT/US2021/027314 dated Jul. 6, 2021.
International Search Report and Written Opinion from International Application No. PCT/US2021/027422 dated Aug. 12, 2021.
International Search Report and Written Opinion from International Application No. PCT/US2021/027425 dated Aug. 11, 2021.
International Search Report and Written Opinion from International Application No. PCT/US2021/027913 dated Jul. 12, 2021.
International Search Report and Written Opinion from International Application No. PCT/US2021/027917 dated Aug. 19, 2021.
International Search Report and Written Opinion from International Application No. PCT/US2021/039866 dated Oct. 7, 2021.
International Search Report and Written Opinion from International Application No. PCT/US2021/043893 dated Nov. 22, 2021.
International Search Report and Written Opinion from International Application No. PCT/US2021/044699 dated Nov. 22, 2021.
International Search Report and Written Opinion from International Application No. PCT/US2021/045188 dated Jan. 26, 2022.
International Search Report and Written Opinion from International Application No. PCT/US2021/047536 dated Dec. 23, 2021.
International Search Report and Written Opinion from International Application No. PCT/US2021/048211 dated Dec. 22, 2021.
International Search Report and Written Opinion from International Application No. PCT/US2021/048661 dated Feb. 14, 2022.
International Search Report and Written Opinion from International Application No. PCT/US2021/049404 dated Jan. 18, 2022.
International Search Report and Written Opinion from International Application No. PCT/US2021/051456 dated Jan. 19, 2022.
International Search Report and Written Opinion from International Application No. PCT/US2021/053593 dated Apr. 11, 2022.
International Search Report and Written Opinion from International Application No. PCT/US2021/055515 dated Jan. 28, 2022.
International Search Report and Written Opinion from International Application No. PCT/US2021/056566 dated Feb. 11, 2022.
International Search Report and Written Opinion from International Application No. PCT/US2021/060993 dated Mar. 18, 2022.
International Search Report and Written Opinion from International Application No. PCT/US2021/062440 dated Mar. 28, 2022.
International Search Report and Written Opinion from International Application No. PCT/US2022/011108 dated Apr. 22, 2022.
International Search Report and Written Opinion from International Application No. PCT/US2022/011281 dated Apr. 25, 2022.
International Search Report and Written Opinion from International Application No. PCT/US2022/011419 dated Jun. 7, 2022.
International Search Report and Written Opinion from International Application No. PCT/US2022/011421 dated Jun. 13, 2022.
International Search Report and Written Opinion from International Application No. PCT/US2022/012794 dated May 3, 2022.
International Search Report and Written Opinion from International Application No. PCT/US2022/014285 dated Sep. 28, 2022.
International Search Report and Written Opinion from International Application No. PCT/US2022/014749 dated Sep. 28, 2022.
International Search Report and Written Opinion from International Application No. PCT/US2022/015026 dated Oct. 31, 2022.
International Search Report and Written Opinion from International Application No. PCT/US2022/015045 dated Sep. 9, 2022.
International Search Report and Written Opinion from International Application No. PCT/US2022/015073 dated Sep. 8, 2022.
International Search Report and Written Opinion from International Application No. PCT/US2022/015418 dated Nov. 11, 2022.
International Search Report and Written Opinion from International Application No. PCT/US2022/015420 dated Nov. 18, 2022.
International Search Report and Written Opinion from International Application No. PCT/US2022/015471 dated May 16, 2022.
International Search Report and Written Opinion from International Application No. PCT/US2022/015492 dated Apr. 26, 2022.

(56) References Cited

OTHER PUBLICATIONS

International Search Report and Written Opinion from International Application No. PCT/US2022/015781 dated May 6, 2022.
International Search Report and Written Opinion from International Application No. PCT/US2022/016942 dated Jun. 8, 2022.
International Search Report and Written Opinion from International Application No. PCT/US2022/018159 dated Dec. 12, 2022.
International Search Report and Written Opinion from International Application No. PCT/US2022/018170 dated May 31, 2022.
International Search Report and Written Opinion from International Application No. PCT/US2022/019254 dated Jun. 7, 2022.
International Search Report and Written Opinion from International Application No. PCT/US2022/019480 dated Jun. 13, 2022.
International Search Report and Written Opinion from International Application No. PCT/US2022/021103 dated Jun. 23, 2022.
International Search Report and Written Opinion from International Application No. PCT/US2022/022111 dated Oct. 26, 2022.
International Search Report and Written Opinion from International Application No. PCT/US2022/023594 dated Jul. 12, 2022.
International Search Report and Written Opinion from International Application No. PCT/US2022/026667 dated Aug. 22, 2022.
International Search Report and Written Opinion from International Application No. PCT/US2022/030685 dated Oct. 31, 2022.
International Search Report and Written Opinion from International Application No. PCT/US2022/031032 dated Sep. 9, 2022.
International Search Report and Written Opinion from International Application No. PCT/US2022/032424 dated Oct. 11, 2022.
International Search Report and Written Opinion from International Application No. PCT/US2022/034457 dated Oct. 12, 2022.
International Search Report and Written Opinion from International Application No. PCT/US2022/034744 dated Dec. 9, 2022.
International Search Report and Written Opinion from International Application No. PCT/US2022/039018 dated Jan. 10, 2023.
International Search Report and Written Opinion from International Application No. PCT/US2022/039022 dated Jan. 10, 2023.
International Search Report and Written Opinion from International Application No. PCT/US2022/039711 dated Jan. 12, 2023.
International Search Report and Written Opinion from International Application No. PCT/US2022/039714 dated Nov. 22, 2022.
International Search Report and Written Opinion from International Application No. PCT/US2022/041085 dated Mar. 16, 2023.
International Search Report and Written Opinion from International Application No. PCT/US2022/041688 dated Nov. 21, 2022.
International Search Report and Written Opinion from International Application No. PCT/US2022/042719 dated Dec. 5, 2022.
International Search Report and Written Opinion from International Application No. PCT/US2022/042725 dated Dec. 19, 2022.
International Search Report and Written Opinion from International Application No. PCT/US2022/043818 dated Mar. 24, 2023.
International Search Report and Written Opinion from International Application No. PCT/US2022/044107 dated Dec. 23, 2022.
International Search Report and Written Opinion from International Application No. PCT/US2022/044208 dated May 8, 2023.
International Search Report and Written Opinion from International Application No. PCT/US2022/044212 dated Jan. 20, 2023.
International Search Report and Written Opinion from International Application No. PCT/US2022/044243 dated Feb. 24, 2023.
International Search Report and Written Opinion from International Application No. PCT/US2022/049300 dated Jun. 6, 2023.
International Search Report and Written Opinion from International Application No. PCT/US2022/050909 dated Jul. 24, 2023.
International Search Report and Written Opinion from International Application No. PCT/US2023/012696 dated Jul. 6, 2023.
Issue Notification for U.S. Appl. No. 14/952,591 dated Jul. 28, 2021.
Issue Notification for U.S. Appl. No. 16/899,956 dated Mar. 29, 2023.
Issue Notification for U.S. Appl. No. 16/905,400 dated Nov. 30, 2022.
Issue Notification for U.S. Appl. No. 17/088,272 dated Jun. 15, 2022.
Issue Notification for U.S. Appl. No. 17/330,657 dated Jun. 22, 2022.
Issue Notification for U.S. Appl. No. 29/624,661 dated Aug. 4, 2021.
Non-Final Office Action for U.S. Appl. No. 16/245,726 dated Jan. 21, 2022.
Non-Final Office Action for U.S. Appl. No. 16/369,676 dated Mar. 31, 2022.
Non-Final Office Action for U.S. Appl. No. 16/433,773 dated Apr. 11, 2023.
Non-Final Office Action for U.S. Appl. No. 16/433,773 dated Apr. 21, 2022.
Non-Final Office Action for U.S. Appl. No. 16/449,039 dated Apr. 27, 2023.
Non-Final Office Action for U.S. Appl. No. 16/449,039 dated Dec. 8, 2021.
Non-Final Office Action for U.S. Appl. No. 16/452,145 dated Mar. 28, 2023.
Non-Final Office Action for U.S. Appl. No. 16/452,145 dated Sep. 28, 2021.
Non-Final Office Action for U.S. Appl. No. 16/452,258 dated Apr. 26, 2023.
Non-Final Office Action for U.S. Appl. No. 16/452,258 dated Sep. 28, 2021.
Non-Final Office Action for U.S. Appl. No. 16/478,180 dated Dec. 20, 2022.
Non-Final Office Action for U.S. Appl. No. 16/478,180 dated Oct. 22, 2021.
Non-Final Office Action for U.S. Appl. No. 16/899,956 dated Sep. 2, 2021.
Non-Final Office Action for U.S. Appl. No. 16/904,868 dated Mar. 15, 2023.
Non-Final Office Action for U.S. Appl. No. 16/904,868 dated Oct. 5, 2021.
Non-Final Office Action for U.S. Appl. No. 16/905,400 dated Apr. 27, 2022.
Non-Final Office Action for U.S. Appl. No. 16/905,400 dated Jul. 22, 2021.
Non-Final Office Action for U.S. Appl. No. 17/051,399 dated Aug. 18, 2023.
Non-Final Office Action for U.S. Appl. No. 17/051,550 dated Dec. 15, 2022.
Non-Final Office Action for U.S. Appl. No. 17/051,585 dated Mar. 29, 2023.
Non-Final Office Action for U.S. Appl. No. 17/179,116 dated Mar. 24, 2023.
Non-Final Office Action for U.S. Appl. No. 17/326,980 dated Jul. 11, 2023.
Non-Final Office Action for U.S. Appl. No. 17/330,657 dated Aug. 11, 2021.
Non-Final Office Action for U.S. Appl. No. 17/444,792 dated Feb. 10, 2023.
Non-Final Office Action for U.S. Appl. No. 17/446,256 dated Apr. 13, 2023.
Non-Final Office Action for U.S. Appl. No. 17/446,654 dated Sep. 8, 2023.
Non-Final Office Action for U.S. Appl. No. 17/448,811 dated Mar. 1, 2023.
Non-Final Office Action for U.S. Appl. No. 17/450,864 dated May 10, 2023.
Non-Final Office Action for U.S. Appl. No. 17/451,345 dated Dec. 7, 2022.
Non-Final Office Action for U.S. Appl. No. 17/451,354 dated May 3, 2023.
Non-Final Office Action for U.S. Appl. No. 17/453,260 dated Mar. 14, 2023.
Non-Final Office Action for U.S. Appl. No. 17/501,591 dated Apr. 25, 2023.
Non-Final Office Action for U.S. Appl. No. 17/646,771 dated Jul. 5, 2023.

(56) References Cited

OTHER PUBLICATIONS

Non-Final Office Action for U.S. Appl. No. 17/653,137 dated Apr. 7, 2023.
Non-Final Office Action for U.S. Appl. No. 17/655,464 dated Mar. 14, 2023.
Non-Final Office Action for U.S. Appl. No. 17/657,474 dated Sep. 12, 2023.
Non-Final Office Action for U.S. Appl. No. 17/661,090 dated Jul. 6, 2023.
Non-Final Office Action for U.S. Appl. No. 17/662,700 dated Jul. 22, 2022.
Non-Final Office Action for U.S. Appl. No. 17/663,330 dated Jun. 29, 2023.
Non-Final Office Action for U.S. Appl. No. 17/664,487 dated Jun. 8, 2023.
Non-Final Office Action for U.S. Appl. No. 18/139,523 dated Aug. 17, 2023.
Non-Final Office Action for U.S. Appl. No. 18/140,751 dated Sep. 14, 2023.
Non-Final Office Action for U.S. Appl. No. 29/741,751 dated Jan. 18, 2022.
Notice of Allowance for U.S. Appl. No. 14/952,591 dated Jul. 8, 2021.
Notice of Allowance for U.S. Appl. No. 16/245,726 dated Jul. 6, 2023.
Notice of Allowance for U.S. Appl. No. 16/449,039 dated Dec. 15, 2022.
Notice of Allowance for U.S. Appl. No. 16/899,956 dated Apr. 19, 2022.
Notice of Allowance for U.S. Appl. No. 16/899,956 dated Aug. 10, 2022.
Notice of Allowance for U.S. Appl. No. 16/899,956 dated Dec. 1, 2022.
Notice of Allowance for U.S. Appl. No. 16/899,956 dated Dec. 29, 2021.
Notice of Allowance for U.S. Appl. No. 16/905,400 dated Aug. 17, 2022.
Notice of Allowance for U.S. Appl. No. 17/088,272 dated Aug. 5, 2021.
Notice of Allowance for U.S. Appl. No. 17/088,272 dated Mar. 4, 2022.
Notice of Allowance for U.S. Appl. No. 17/088,272 dated Nov. 24, 2021.
Notice of Allowance for U.S. Appl. No. 17/330,657 dated Mar. 16, 2022.
Notice of Allowance for U.S. Appl. No. 17/330,657 dated Nov. 26, 2021.
Notice of Allowance for U.S. Appl. No. 17/461,036 dated Feb. 22, 2023.
Notice of Allowance for U.S. Appl. No. 17/461,036 dated Jun. 30, 2023.
Notice of Allowance for U.S. Appl. No. 17/461,036 dated Oct. 6, 2022.
Notice of Allowance for U.S. Appl. No. 17/662,700 dated Jul. 28, 2023.
Notice of Allowance for U.S. Appl. No. 17/662,700 dated Mar. 28, 2023.
Notice of Allowance for U.S. Appl. No. 17/663,046 dated Jan. 30, 2023.
Notice of Allowance for U.S. Appl. No. 18/299,788 dated Jul. 24, 2023.
Notice of Allowance for U.S. Appl. No. 29/741,751 dated Jun. 9, 2022.
Restriction Requirement for U.S. Appl. No. 16/433,773 dated Dec. 7, 2021.
Restriction Requirement for U.S. Appl. No. 17/051,600 dated Sep. 21, 2023.
Restriction Requirement for U.S. Appl. No. 17/326,980 dated Mar. 20, 2023.
Restriction Requirement for U.S. Appl. No. 17/446,256 dated Jan. 23, 2023.
Restriction Requirement for U.S. Appl. No. 17/645,821 dated Jul. 12, 2023.
Restriction Requirement for U.S. Appl. No. 17/646,771 dated Apr. 6, 2023.
Restriction Requirement for U.S. Appl. No. 17/657,474 dated Jun. 30, 2023.
Text Messages to Lorena Eckert Re Prototype PureWick Holder dated Apr. 16, 2022.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/384,196 filed Dec. 19, 2016.
U.S. Appl. No. 16/245,726, filed Jan. 11, 2019.
U.S. Appl. No. 17/378,015, filed Jul. 16, 2021.
U.S. Appl. No. 17/394,055, filed Aug. 4, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 dated Aug. 30, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,487, filed May 23, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.

(56) References Cited

OTHER PUBLICATIONS

U.S. Appl. No. 18/246,121, filed Mar. 21, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/485,578, filed Apr. 14, 2017.
U.S. Appl. No. 62/853,279, filed May 28, 2019.
U.S. Appl. No. 62/864,656, filed Jun. 21, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149 filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187 filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 63/008,112, filed Apr. 10, 2020.
U.S. Appl. No. 63/030,685, filed May 27, 2020.
U.S. Appl. No. 63/047,374, filed Jul. 2, 2020.
U.S. Appl. No. 63/067,542, filed Aug. 19, 2020.
U.S. Appl. No. 63/073,545, filed Sep. 2, 2020.
U.S. Appl. No. 63/073,553, filed Sep. 2, 2020.
U.S. Appl. No. 63/094,498, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/150,640, filed Feb. 18, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,328, filed Sep. 7, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
U.S. Appl. No. 63/308,190, filed Feb. 9, 2022.
*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"External Urine Management for Female Anatomy", https://www.stryker.com/us/en/sage/products/sage-primafit.html, Jul. 2020, 4 pages.
"GSA Price List", Omni Medical, Apr. 2011, 2 pages.
"High Absorbancy Cellulose Acetate Electrospun Nanofibers for Feminine Hygiene Application" , https://www.sciencedirect.com/science/article/abs/pii/S2352940716300701?via%3Dihub , Jul. 2016, 3 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"Letter to Mark Harvie of Omni Measurement Systems", Department of Veterans Affairs, Nov. 1, 2007, 11 pages.
"Making Women's Sanitary Products Safer and Cheaper", https://www.elsevier.com/connect/making-womens-sanitary-products-safer-and-cheaper, Sep. 2016, 10 pages.

(56) References Cited

OTHER PUBLICATIONS

"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Revised AMXDmax Advanced Mission Extender Device User & Maintenance Guide", Omni Medical Systems, Oct. 8, 2019, 52 pages.
"Rising Warrior Insulated Gallon Jug Cover", https://www.amazon.com/Rising-Warrior-Insulated-Sleeve, 2021, 2 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"Vinyl Dust Cover, Janome #741811000, Janome, Sewing Parts Online", https://www.sewingpartsonline.com/vinyl-dust-cover-janome-74181000, 2020, 2 pages.
Ali, "Sustainability Assessment: Seventh Generation Diapers versus gDiapers", The University of Vermont, Dec. 6, 2011, pp. 1-31.
Autumn, et al., "Frictional adhesion: a new angle on gecko attachment", The Journal of Experimental Biology, 2006, pp. 3569-3579.
Cañas, et al., "Effect of nano- and micro-roughness on adhesion of bioinspired micropatterned surfaces", Acta Biomaterialia 8, 2012, pp. 282-288.
Chaudhary, et al., "Bioinspired dry adhesive: Poly(dimethylsiloxane) grafted with poly(2-ethylhexyl acrylate) brushes", European Polymer Journal, 2015, pp. 432-440.
Dai, et al., "Non-sticky and Non-slippery Biomimetic Patterned Surfaces", Journal of Bionic Engineering, Mar. 2020, pp. 326-334.
Espinoza-Ramirez, "Nanobiodiversity and Biomimetic Adhesives Development: From Nature to Production and Application", Journal of Biomaterials and Nanobiotechnology, pp. 78-101, 2019.

Hwang, et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong, et al., "A nontransferring dry adhesive with hierarchical polymer nanohairs", PNAS, Apr. 7, 2009, pp. 5639-5644.
Jeong, et al., "Nanohairs and nanotubes: Efficient structural elements for gecko-inspired artificial dry adhesives", Science Direct, 2009, pp. 335-346.
Karp, et al., "Dry solution to a sticky problem", Nature, 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Merriam-Webster Dictionary, "Embed Definition & Meaning", https://www.merriam-webster.com/dictionary/embed last accessed Aug. 3, 2023, 2003.
Parness, et al., "A microfabricated wedge-shaped adhesive array displaying gecko-like dynamic adhesion, directionality", J.R. Soc. Interface, 2009, pp. 1223-1232.
Pieper, et al., "An external urine-collection device for women: A clinical trial", Journal of ER Nursing, vol. 20, No. 2, Mar./Apr. 1993, pp. 51-55.
Tsipenyuk, et al., "Use of biomimetic hexagonal surface texture in friction against lubricated skin", Journal of The Royal Society—Interface, 2014, pp. 1-6.
Vinas, "A Solution For An Awkward—But Serious—Subject", http://www.aero-news.net/index.cfm?do=main.textpost&id=69ae2bb1-838b-4098-a7b5-7flbb2505688 last accessed Feb. 8, 2021.

\* cited by examiner

FLUID COLLECTION DEVICES, SYSTEMS, AND METHODS

CROSS-REFERENCE TO RELATED APPLICATIONS

This application is U.S. Nationalization of PCT International Application No. PCT/US2019/029610 filed on 29 Apr. 2019, which claims priority to U.S. Provisional Application No. 62/665,321 filed on 1 May 2018, the disclosure of each of which is incorporated herein in its entirety by this reference.

BACKGROUND

An individual may have limited or impaired mobility such that typical urination processes are challenging or impossible. For example, the individual may have surgery or a disability that impairs mobility. In another example, the individual may have restricted travel conditions such as those experience by pilots, drivers, and workers in hazardous areas. Additionally, fluid collection from the individual may be needed for monitoring purposes or clinical testing.

Bed pans and urinary catheters, such as a Foley catheter, can be used to address some of these circumstances. However, bed pans and urinary catheters have several problems associated therewith. For example, bed pans can be prone to discomfort, spills, and other hygiene issues. Urinary catheters be can be uncomfortable, painful, and can cause urinary tract infections.

Thus, users and manufacturers of fluid collection devices continue to seek new and improved devices, systems, and methods to collect urine.

SUMMARY

Embodiments disclosed herein are related to devices, systems, and methods of using fluid collection devices. In an embodiment, a fluid collection device is disclosed. The fluid collection device includes a fluid collection member. The fluid collection member includes a fluid impermeable barrier at least partially defining a chamber, the fluid impermeable barrier also defining an opening extending therethrough, the opening configured to be positioned adjacent to a female urethra or have a male urethra positioned therethrough. The fluid collection member includes wicking material disposed at least partially within the chamber. The fluid collection member includes a conduit disposed within the chamber, the conduit including an inlet positioned within the fluid collection device and an outlet configured to be in fluid communication with a portable vacuum source. The fluid collection device includes at least one flange extending outwardly from the fluid collection member, the at least one flange including an adhesive member thereon.

In an embodiment, a fluid collection system is disclosed. The fluid collection system includes a fluid storage container configured to hold a fluid. The fluid collection system includes a fluid collection device in fluid communication with the fluid storage container. The fluid collection device includes a fluid collection member. The fluid collection member includes a fluid impermeable barrier at least partially defining a chamber, the fluid impermeable barrier also defining an opening extending therethrough, the opening configured to be positioned adjacent to a female urethra or have a male urethra positioned therethrough. The fluid collection member includes a wicking material disposed at least partially within the chamber. The fluid collection member includes a conduit disposed within the chamber, the conduit including an inlet positioned within the fluid collection device and an outlet configured to be in fluid communication with a portable vacuum source. The fluid collection device includes at least one flange extending outwardly from the fluid collection member, the at least one flange including an adhesive member thereon. The fluid collection system includes a vacuum source in fluid communication with one or more of the fluid storage container or the fluid collection device, the vacuum source configured to draw fluid from the fluid collection device.

In an embodiment, a method to collect fluid is disclosed. The method includes positioning an opening of a fluid collection device adjacent to a female urethra or around a male urethra of a user, the opening defined by a fluid impermeable barrier of the fluid collection device. The method includes positioning securing the fluid collection device to the user. The method includes positioning receiving fluid from the female urethra or male urethra into a chamber of the fluid collection device, the chamber of the fluid collection device at least partially defined by the fluid impermeable barrier.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1:
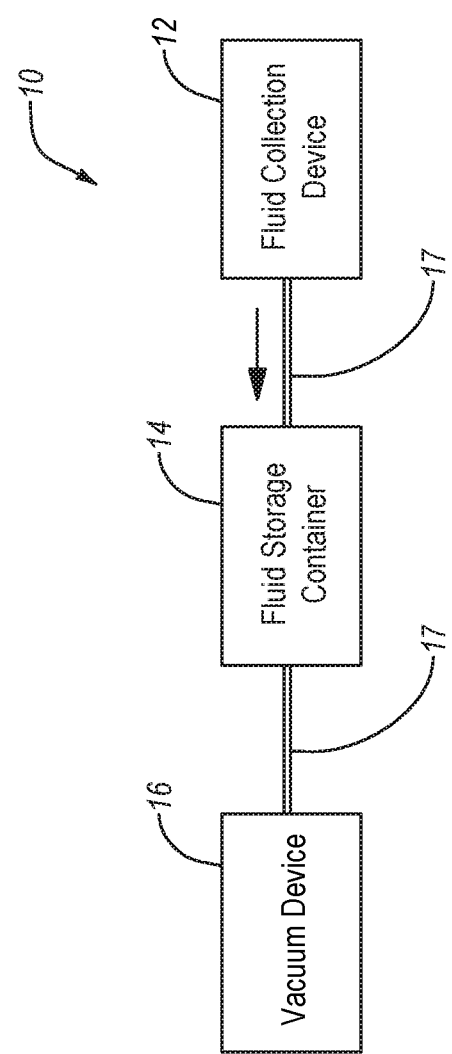
FIG. 1 is a block diagram of a system for fluid collection, according to an embodiment.

Embodiments disclosed herein are related to devices, systems, and methods of using fluid collection devices and systems. The devices, systems, and methods of using fluid collection devices and systems include at least one flange extending from the fluid collection device where the at least one flange is positioned to attach to the skin of a user and align the fluid collection device with one or more anatomical structures of the user (e.g., urethra). The devices, systems, and methods of using fluid collection devices and systems include a portable vacuum source to remove urine from the fluid collection device. The portable vacuum source may allow for portable usage of the systems and methods herein such as in non-hospital environments.

In an embodiment, a fluid collection device includes a fluid impermeable barrier that at least partially defines a chamber. The fluid impermeable barrier also defines an opening extending therethrough that is configured to be positioned adjacent to a female urethra or have a male urethra positioned therethrough. The fluid collection device also includes a tube having a channel extending between an inlet and outlet thereof. The inlet is configured to be coupled to a suction source and the outlet is configured to be fluidly coupled to (e.g., in fluid communication with) a fluid storage (vessel or container). The outlet is positioned downstream from the inlet. The channel also defines at least one aperture therein that fluidly couples an interior of the channel to the rest of the chamber.

The fluid collection devices disclosed herein are configured to collect fluid(s) from an individual. The fluid(s) collected by the fluid collection devices can include urine. The fluid(s) collected by the fluid collection devices can also include at least one of vagina discharge, penile discharge, reproductive fluids, blood, sweat, or other bodily fluids.

The fluid collection devices disclosed herein are configured to be used in fluid collection systems. The fluid collection systems disclosed herein include a gas source. Systems that include a gas source can, in some embodiments, resolve several problems associated with systems that include a vacuum source. For example, a system that includes a vacuum source draws fluid(s) towards the vacuum source and deposits most of the fluid(s) in a fluid storage container before the fluid(s) can reach the vacuum source. However, a small quantity of fluid(s) (e.g., vapor from the fluid) can still reach the vacuum source, which can contaminate and/or damage (e.g., rust) the vacuum source. Additionally, a large quantity of the fluid(s) can reach the vacuum source when the fluid storage container is substantially full. However, a system that includes a gas source moves the fluid(s) away from the gas source, thereby preventing contamination and/or damage. For example, a gas source may be used to create a vacuum by flowing a gas past a connected end of the conduit at a perpendicular or oblique angle to the conduit to create a vacuum in the conduit. The fluids are pulled up the conduit and into the gas flow in the direction of the gas flow, which is away from the gas source. In another embodiment, systems that include a vacuum source cannot be used in environments that do not include an available vacuum source (e.g., the environment does not include a vacuum source or the vacuum source is being used). As such, systems that include a gas source can be used in environments that do not include an available vacuum source. A liquid source can be used to create and implement a vacuum in the same way as the gas source. The vacuum source or gas source can be utilized with any of the devices or systems disclosed herein to remove a fluid therefrom.

FIG. 1 is a block diagram of a system 10 for fluid collection, according to an embodiment. The system 10 includes a fluid collection device 12, a fluid storage container 14, and a vacuum source 16. The fluid collection device 12, the fluid storage container 14, and the vacuum source 16 may be in fluid communication with (e.g., fluidly coupled to) each other via one or more conduits 17. For example, fluid collection device 12 may be in fluid communication with one or more of the fluid storage container 14 or the vacuum source via the conduit 17. Fluid (e.g., urine or other bodily fluids) collected in the fluid collection device 12 may be removed from the fluid collection device 12 via the conduit 17 which protrudes into an interior region of the fluid collection device 12. For example, a first open end of the conduit 17 may extend into the fluid collection device 12 to a reservoir therein. The second open end of the conduit 17 may extend into the fluid storage container 14 or the vacuum source 16. The suction force may be introduced into the interior region of the fluid collection device 12 via the first open end of the conduit 17 responsive to a suction (e.g., vacuum) force applied at the second end of the conduit 17. The suction force may be applied to the second open end of the conduit 17 by the vacuum source 16 either directly or indirectly.

The suction force may be applied indirectly via the fluid storage container 14. For example, the second open end of the conduit 17 may be disposed within the fluid storage container 14 and an additional conduit 17 may extend from the fluid storage container 14 to the vacuum source 16. Accordingly, the vacuum source 16 may apply suction to the fluid collection device 12 via the fluid storage container 14. The suction force may be applied directly via the fluid storage container 14. For example, the second open end of the conduit 17 may be disposed within the vacuum source 16. An additional conduit 17 may extend from the vacuum source 16 to a point outside of the fluid collection device 12, such as to the fluid storage container 14. In such examples, the vacuum source 16 may be disposed between the fluid collection device 12 and the fluid storage container 14.

The fluid collection device 12 may be shaped and sized to be positioned adjacent to a female urethra. For example and as described in more detail below, the fluid collection device 12 may include a fluid collection member and at least one flange positioned and equipped to attach to the skin of a user and align the fluid collection member in a selected portion of the anatomy of the user (e.g., adjacent to or on the urethra or vagina). For example, the at least one flange may include an adhesive for reversibly attaching to the skin of the user and may be positioned on the fluid collection member to align an opening of the fluid collection member with the vagina (e.g., on or over the urethra or between the labia) of a female user.

The fluid collection member of the fluid collection device 12 may include a fluid impermeable barrier at least partially defining a chamber (e.g., interior region of the fluid collection device member) of the fluid collection device 12. The fluid impermeable barrier also defines an opening extending therethrough from the external environment. The opening may be positioned on the fluid collection member to be aligned adjacent to a female urethra. The fluid collection member of the fluid collection device 12 may include a fluid permeable membrane disposed within the fluid impermeable barrier. The fluid collection member of the fluid collection device 12 may include a fluid permeable support disposed within the fluid permeable membrane. The conduit 17 may extend into the fluid collection device 12 at a first end region, through one or more of the fluid impermeable barrier, fluid permeable membrane, or the fluid permeable support to a second end region of the fluid collection member of the fluid collection device 12. Exemplary fluid collection devices for use with the systems and methods herein are described in more detail below.

In examples, the fluid storage container 14 may include a bag (e.g., drainage bag), a bottle or cup (e.g., collection jar), or any other enclosed container for storing bodily fluid(s) such as urine. In examples, the conduit 17 may extend from the fluid collection device 12 and attach to the fluid storage container 14 at a first point therein. An additional conduit 17 may attach to the fluid storage container 14 at a second point thereon and may extend and attach to the vacuum source 16. For example, the fluid storage container 14 may include a container in fluid communication with a first conduit section that is also in fluid communication with the fluid collection member of the fluid collection device 12. The container may be in fluid communication with a second section of the conduit 17 that is also in fluid communication with a vacuum source. In such examples, the vacuum source 16 may provide a vacuum/suction through the container to the fluid collection member to provide suction in the chamber of the fluid collection member. Accordingly, a vacuum (e.g., suction) may be drawn through fluid collection device 12 via the fluid storage container 14. As the fluid is drained from the chamber, the fluid may travel through the first section of conduit to the fluid storage container where it may be retained. Fluid, such as urine, may be drained from the fluid collection device 12 using the vacuum source 16.

In some examples, the vacuum source 16 may include a portable vacuum source. In examples, the portable vacuum source may be disposed in or on the fluid collection device 12. In such examples, the conduit 17 may extend from the fluid collection device and attach to the (portable) vacuum source 16 at a first point therein. An additional conduit 17 may attach to the vacuum source 16 at a second point thereon and may extend out of the fluid collection device 12, and may attach to the fluid storage container 14. Accordingly, a vacuum (e.g., suction) may be drawn through fluid collection device 12 via the fluid storage container 14.

The vacuum source 16 may include one or more of a vacuum line plumbed into patient care facility, a manual vacuum pump, and electric vacuum pump, a diaphragm pump, a centrifugal pump, a displacement pump, a magnetically driven pump, a peristaltic pump, or any pump configured to produce a vacuum. The vacuum source 16 may provide a vacuum or suction to remove fluid from the fluid collection member of the fluid collection device 12. In examples, the vacuum source 16 may be powered by one or more of a power cord (e.g., connected to a power socket), one or more batteries, or even manual power (e.g., a hand operated vacuum pump). In examples, the vacuum source 16 (e.g., portable vacuum source) may be sized and shaped to fit outside of, on, or within the fluid collection device 12. For example, the vacuum source 16 (e.g., portable vacuum source) may include one or more miniaturized pumps or one or more micro pumps. The vacuum sources 16 disclosed herein may include one or more of a switch, a button, a plug, a remote, or any other device suitable to activate the vacuum source 16. It should be understood that the vacuum sources 16 disclosed herein may provide a portable means of providing a suction or vacuum that allows use of the devices and systems herein outside of hospital or care facility environments where vacuum lines are plumbed into patient rooms or large (e.g., larger or heavier than a patient can readily carry) vacuum sources are located. For example, a portable vacuum source may be small and light enough to be carried by a user (e.g., patient) or aid (e.g., nurse) during transportation of the user.

Figure 2A:
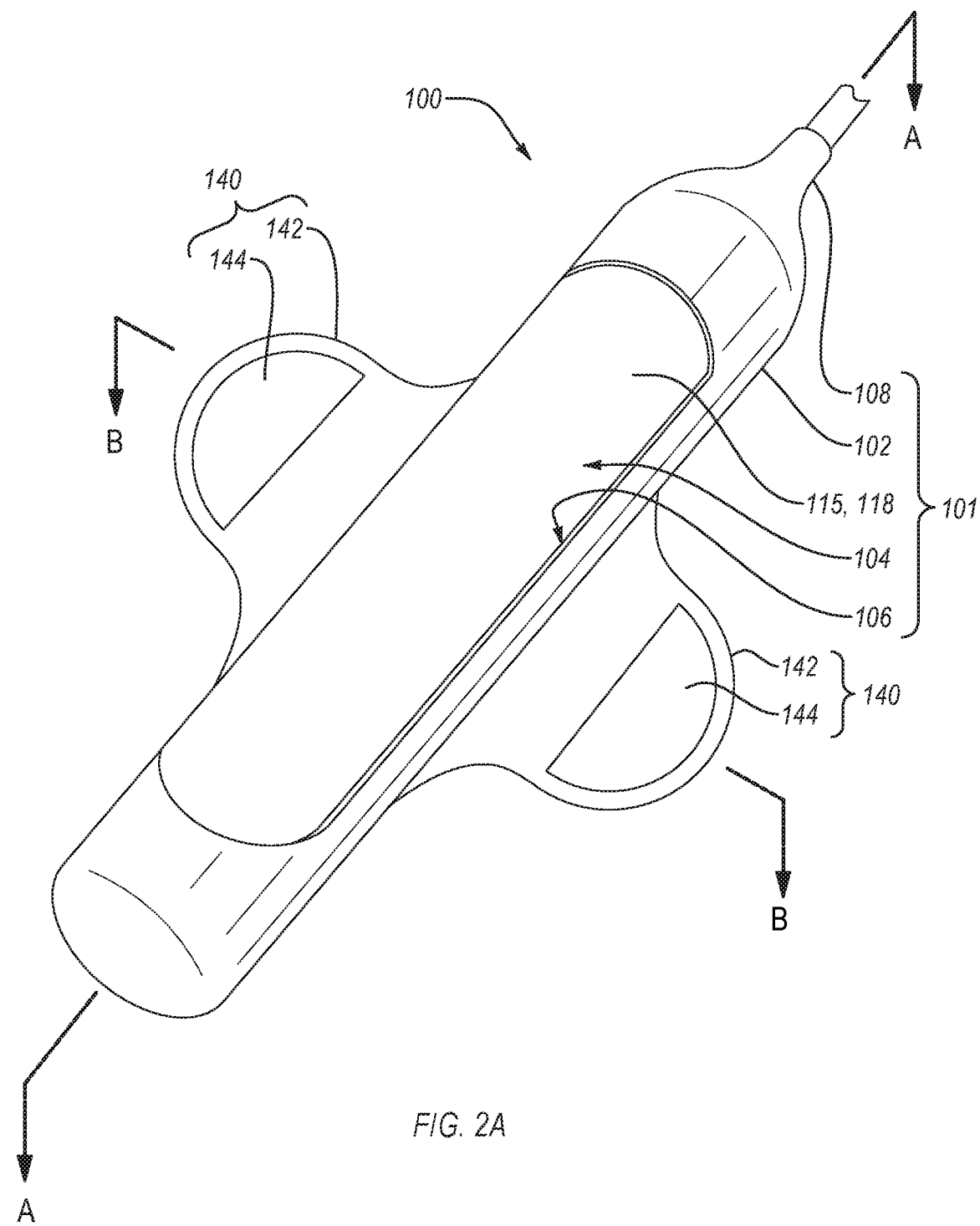
FIG. 2A is an isometric view of a fluid collection device, according to an embodiment.

FIG. 2A is an isometric view of a fluid collection device 100, according to an embodiment. The fluid collection device 100 includes a fluid collection member 101 and at least one flange 140 extending from the fluid collection member 101. In some examples, the fluid collection member 101 may be substantially cylindrical, ellipsoid, prismatic, or any other shape suitable for complementing or contouring to the vaginal region of a female subject. The fluid collection member 101 may include a fluid impermeable barrier 102, wicking material 115, and a conduit 108. The wicking material 115 may be disposed at least partially within the fluid impermeable barrier 102. The conduit 108 may be at least partially disposed with wicking material 115.

The fluid impermeable barrier 102 at least partially defines at least a portion of an outer surface of the fluid collection member 101. The fluid impermeable barrier 102 at least partially defines a chamber 104 therein (e.g., interior region of the fluid collection member 101) and an opening 106. The opening 106 is formed in and extends through the fluid impermeable barrier 102, thereby enabling fluid(s) to enter the chamber 104 from outside of the fluid collection member 101 of the fluid collection device 100. The opening 106 can be configured to be positioned adjacent to a female urethra, such as between the labia majora of a female user.

The fluid impermeable barrier 102 may also temporarily retain or store fluid(s) in the chamber 104. For example, the fluid impermeable barrier 102 can be formed of any suitable fluid impermeable materials, such as a fluid impermeable polymer (e.g., silicone, polypropylene, polyethylene, polyethylene terephthalate, polyurethane, a polycarbonate, polyvinyl chloride, latex, silicone, etc.), a metal film, another suitable material, or combinations thereof. As such, the fluid impermeable barrier 102 may prevent at least some of the fluid(s) from exiting the portions of the chamber 104 that are spaced from the opening 106.

In an embodiment, the fluid impermeable barrier 102 can be air permeable and fluid impermeable. In such an embodiment, the fluid impermeable barrier 102 can be formed of a hydrophobic material that defines a plurality of pores. In an example, one or more portions of at least an outer surface of the fluid impermeable barrier 102 can be formed from a soft and/or smooth material thereby reducing chafing of the skin of the user. The fluid impermeable barrier 102 may include markings thereon, such as one or more markings to aid a user in aligning the device 100 on the wearer. For example, a line on the fluid impermeable barrier 102 (e.g., opposite the opening 106) may allow a healthcare professional to align the opening 106 over the urethra of the wearer. In examples, the markings may include one or more of alignment guide or an orientation indicator, such as a stripe or hashes. Such markings may be positioned to align the device 100 to one or more anatomical features such as a pubic bone, etc.

The wicking material 115 may be disposed at least partially within the fluid impermeable barrier 102. The wicking material 115 may include permeable material designed to wick or allow fluid to pass therethrough. The permeable properties referred to herein can be wicking, capillary action, diffusion, or other similar properties or processes, and are referred to herein as "permeable" and/or "wicking." Such "wicking" may not include absorption into the wicking material. The wicking material 115 may collect the fluid that travels through the opening 106. The wicking material 115 may include more than one material, such as a plurality of materials. The plurality of materials may include a plurality of layers concentrically disposed within one another. The concentrically disposed layers of wicking materials may exhibit a gradient of wicking, such as where the innermost wicking material includes the greatest or least wicking ability of the plurality of materials.

In examples, the wicking material 115 may include one or more of a fluid permeable support (FIGS. 3-8) or a fluid permeable membrane 118. For example, the fluid collection member 101 of the fluid collection device 100 can include a fluid permeable membrane 118 disposed in the chamber 104. The fluid permeable membrane 118 can cover at least a portion (e.g., all) of the opening 106. The fluid permeable membrane 118 can be configured to wick any fluid away from the opening 106, thereby preventing the fluid from escaping the chamber 104. The fluid permeable membrane 118 can also wick the fluid generally towards an interior of the chamber 104, as discussed in more detail below. The fluid permeable membrane 118 can include any material that can wick the fluid. For example, the fluid permeable membrane 118 can include fabric, such as a gauze (e.g., a silk, linen, polyester, or cotton gauze), another soft fabric (e.g., jersey knit fabric or the like), or another smooth fabric (e.g., rayon, satin, or the like). In some examples, the fluid permeable membrane 118 can include an open cell foam. Forming the fluid permeable membrane 118 from gauze, soft fabric, and/or smooth fabric can reduce chafing caused by the fluid collection device 100.

The fluid collection device 100 can include a fluid permeable support 120 (FIGS. 3-8) disposed in the chamber 104. The fluid permeable support 120 may support the fluid permeable membrane 118 since the fluid permeable membrane 118 can be formed from a foldable, flimsy, or otherwise easily deformable material. For example, the fluid permeable support 120 can be positioned such that the fluid permeable membrane 118 is disposed between the fluid permeable support and the fluid impermeable barrier 102. As such, the fluid permeable support 120 can support and maintain the position of the fluid permeable membrane 118. The fluid permeable support 120 can be formed from any fluid permeable material that is less deformable than the fluid permeable membrane 118. For example, the fluid permeable support 120 can include a porous nylon structure or an open cell foam. In embodiments, the fluid permeable support can be omitted from the fluid collection device 100.

In some embodiments, the wicking material 115 (e.g., one or more of the fluid permeable membrane 118 or the fluid permeable support) can at least substantially completely fill portions of the chamber 104 that are not occupied by the conduit 108. For example, the wicking material 115 may fill the portions of the chamber 104 that are not occupied by the conduit 108. In some examples, the fluid permeable membrane 118 and the fluid permeable support may not substantially completely fill the portions of the chamber 104 that are not occupied by the conduit 108. In such examples, the fluid collection device 100 may include the reservoir (e.g., void space) disposed in the chamber 104. The reservoir may include a void space between the wicking material in the chamber 104 and the interior surface of the fluid impermeable barrier 102. At least some of the fluid absorbed by the wicking material 115 may drain out of the wicking material 115 and collect in the reservoir.

The fluid collection member 101 of the fluid collection device 100 may also include conduit 108 that is at least partially disposed in the chamber 104. The conduit 108 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In examples, the conduit 108 may include silicon or latex. The conduit 108 (e.g., a tube) includes an inlet at a first end region and an outlet at a second end region positioned downstream from the inlet. The conduit 108 places an interior region of the chamber 104 in fluid communication with one or more of the fluid storage container (FIG. 1) or the vacuum source (FIG. 1). The fluid may be removed from the chamber 104 via the conduit 108. As suction or vacuum force is applied or formed in the conduit 108 by the vacuum source (FIG. 1), the fluid in the chamber 104 may be drawn into the inlet and out of the fluid collection member 101 via the conduit 108.

In examples, the conduit 108 may be disposed in an innermost or gravimetrically low spot in the chamber 104. For example, the conduit 108 may extend far enough into the chamber 104 to position the inlet in a gravimetrically low spot of the chamber 104 (e.g., fluid reservoir within the interior of the fluid collection member 101).

The fluid collection member 101 and components thereof may be deformable (e.g., bendable) responsive to pressure applied thereto. For example, the fluid collection member 101 and the components thereof may bend to conform to the surface of the user, such as when disposed between a garment and the user. In examples, the fluid collection member 101 may bend when disposing proximate to the urethra (e.g., between the labia) when undergarments are pulled on over the fluid collection member 101.

The at least one flange 140 may extend from the fluid collection member 101. The at least one flange may include a flange body 142 and an adhesive member 144 disposed on the flange body 142. In some examples, the at least one flange 140 may include 2 or more flanges (e.g., 4 flanges). The at least one flange 140 may include a first flange body extending a first direction away from the fluid collection member 101 and a second flange body extending away from the fluid collection member 101 in a second direction, wherein the first and second directions are substantially opposite one another (e.g., at least 120° apart). The at least one flange 140 may extend along at least a portion of the longitudinal length of fluid collection member 101. For example, the at least one flange 140 may have a width, as viewed parallel to the plane B-B, of least 5% (e.g., at least 10%, at least 20%, at least 30%, at least 40%, at least 50%, or less than 60%) of the longitudinal length of the fluid collection member 101. In examples, the width of the flange 140 may be at least 1 cm, such as 2 cm, 5 cm, 10 cm, 15 cm, 20 cm, 30 cm, or in a range between any combination of the foregoing. The flange 140 (e.g., flange body 142) may extend at least 1 cm away from the fluid collection member 101, such as 1 cm, 3 cm, 5 cm, 10 cm, 15 cm, 20 cm, 25 cm, 30 cm, or in a range between any combination of the foregoing, away from the fluid collection member 101.

In examples, the flange body 142 of the at least one flange 140 may be formed of the same material as the fluid impermeable barrier 102. In examples, the flange body 142 of the at least one flange 140 may be formed from one or more of cloth, paper, plastic, or any other material suitable for deforming responsive to pressure applied thereto and able to withstand moisture without breaking down. For example, the flange body 142 may be formed from thermoplastic elastomer, polyethylene, polyvinyl chloride, ethylene vinyl acetate, polytetrafluoroethylene, latex, silicon, fabric, woven cloth, etc. In examples, the conduit 108 may include silicon or latex. The flange body 142 of the at least one flange 140 may be flexible and may conform to manipulation or movement by a user. The flange body 142 may exhibit any of the dimensions disclosed above for the flange 140.

The flange body 142 may have the adhesive member 144 disposed thereon, such as at a distal portion thereof (e.g., distal from the fluid collection member 101). The adhesive member 144 may be affixed to the flange body 142 by mechanical means such as a staple(s), a clip, hook and loop fasteners, etc.; may be affixed by an adhesive; or may be integrally formed in the flange body 142. The adhesive member 144 may be positioned on the flange body 142 in a position effective to allow the adhesive to be applied to a garment of the skin of the user to maintain a position of the fluid collection member 101 with respect to one or more anatomical features (e.g., proximate to the female urethra or between the labia) of the user. For example, the adhesive member 144 may be positioned on the flange body 142 to allow the at least one flange(s) 140 to adhere to the inner thigh of a user and maintain a position of the associated fluid collection member 101 between the labia of the user 190. In examples, the adhesive member 144 may be flexible or otherwise configured to conform to the anatomical features of the user and accommodate movement of the user.

Figure 2B:
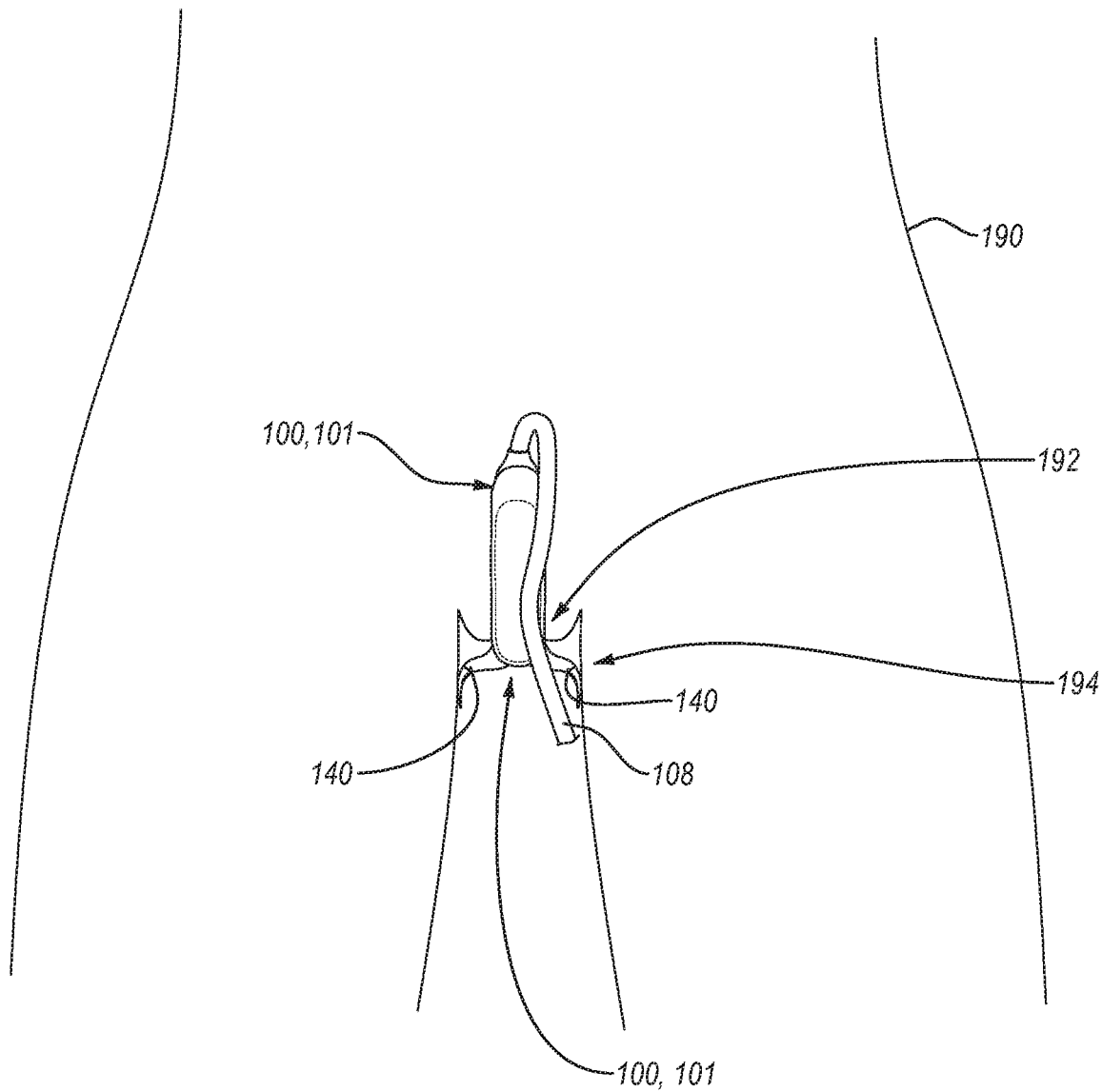
FIG. 2B is a front view of a user with the fluid collection device of FIG. 2A positioned for use, according to an embodiment.

FIG. 2B is a front view of a user 190 with the fluid collection device 100 positioned for use, according to an embodiment. The user 190 may be a female and the fluid collection device 100 may be positioned for use (e.g., collecting urine or other bodily fluids from the vagina). For example, the flanges 140 may be disposed on the fluid collection member 101 in a position to locate the fluid collection member 101 between the labia 192 when the at least one flange 140 is adhered to the inner thigh 194 of the user 190. In examples, the at least one flange 140 can be adhered to the pubic region (e.g., lower abdominal region) of the user 190 to align the fluid collection member over the urethra of the user 190. In some examples, the at least one flange 140 can be adhered to the fabric of a garment worn by the user 190 (e.g., an undergarment). The conduit 108 may be in fluid communication with the fluid storage container or vacuum pump (not shown) to remove any collected fluid(s) from the fluid collection device 100.

Returning to FIG. 2A, the at least one flange body 142 may include the adhesive member 144 disposed thereon. For example, the adhesive member 144 may be facing upward on the flange body 142 (e.g., in the general direction of the fluid collection member 101). In some examples, the flange 140 may additional or alternatively include the adhesive member 144 facing downward on the flange body 142. In examples, the adhesive member 144 may be located on a distal portion of the flange body 142 (e.g., distal from the fluid collection member 101). In examples, the adhesive member 144 may cover at least 5% of the surface area of the flange body 142, such as 5%, 10%, 20%, 30%, 40%, 50%, 60%, 70%, 80%, 90%, or ranges between any combination of the foregoing, of the surface area of the flange body 142.

In examples, the adhesive member 144 may include a glue, contact adhesive, epoxy, hydrogel adhesive, tape, or other adhesive suitable for attaching the flange to skin or fabric. For example, the adhesive may include an acrylate (e.g., methacrylate or epoxy diacrylate) or any other adhesive suitable for use on bandages.

The cross-sectional profiles of the fluid collection devices disclosed herein may vary. For example, a longitudinal cross section is taken along the plane A-A and an axial cross section may be viewed along the plane B-B in FIG. 2A.

Figure 3:
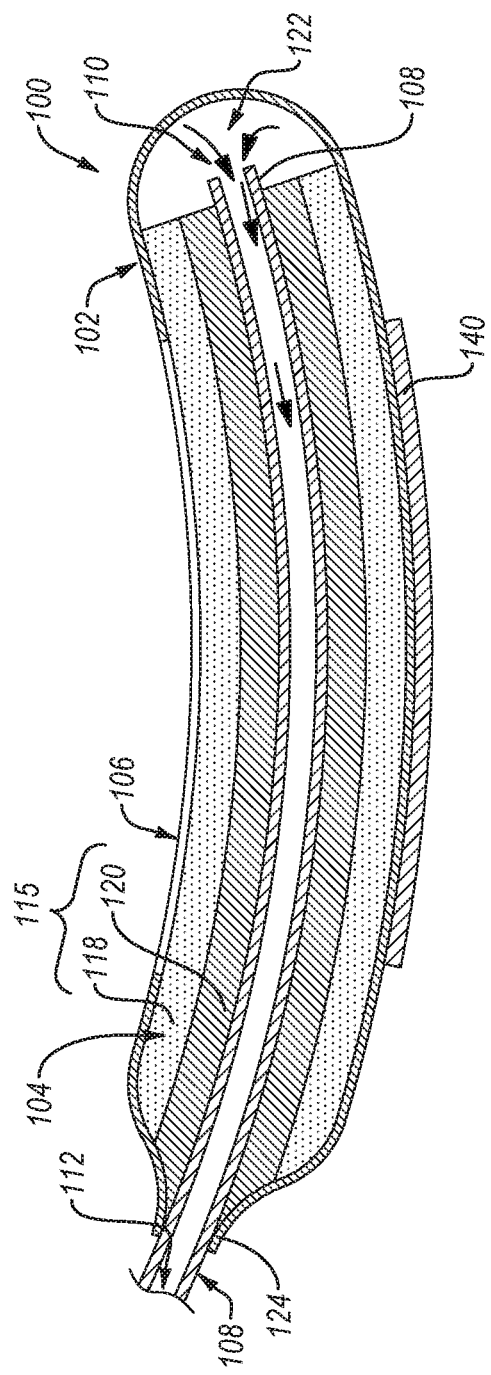
FIGS. 3-5 are schematic cross-sectional views of fluid collection devices taken along the plane A-A of FIG. 2A, according to embodiments.

FIG. 3 is a schematic cross-sectional view of the fluid collection device 100 taken along the plane A-A of FIG. 2A, according to an embodiment. The fluid collection device 100 is an example of a female fluid collection device 100 sized, shaped, and otherwise configured to receive fluid(s) from a female user. The fluid collection device 100 includes the fluid collection member 101 and the at least one flange 140. The fluid collection member 101 includes the fluid impermeable barrier 102. The fluid impermeable barrier 102 at least partially defines the chamber 104 (e.g., interior region) and the opening 106. The opening 106 is formed in and extends through the fluid impermeable barrier 102, thereby enabling fluid(s) to enter the chamber 104 from outside of the fluid collection device 100. The opening 106 can be configured to be positioned adjacent to a female urethra. The opening 106 can be positioned on an upward facing portion of the fluid collection member 101 (e.g., region substantially opposite the flanges 140). The fluid collection device 100 also includes conduit 108 that is at least partially disposed in the chamber 104. The conduit 108 (e.g., a tube) includes an inlet 110 at a first end region and an outlet 112 at a second end region positioned downstream from the inlet 110. The conduit 108 places the chamber 104 in fluid communication with the fluid storage container (not shown) or the vacuum source (not shown).

In the illustrated embodiment, the conduit 108 is at least partially disposed in the chamber 104. For example, the conduit 108 may extend into the fluid impermeable barrier 102 from the first end region (e.g., proximate to the outlet 112) and may extend to the second end region (e.g., opposite the first end region) to a point proximate to the reservoir 122 such that the inlet 110 is in fluid communication with the reservoir 122. The fluid collected in the fluid collection member 101 may be removed from the interior region of the chamber 104 via the conduit 108. The conduit 108 may include a flexible material such as plastic tubing (e.g., medical tubing) as disclosed herein. In some examples, the conduit 108 may include one or more portions that are resilient, such as to by having one or more of a diameter or wall thickness that allows the conduit to be flexible.

The fluid collection member 101 may be positioned proximate to the female urethra (e.g., on or between the labia) and urine may enter the chamber 104 of the fluid collection member 101 via the opening 106. The fluid collection member 101 receives the fluid(s) into the chamber 104 via the opening 106. For example, the opening 106 can exhibit an elongated shape that is sized and positioned to extend from a first location below the urethral opening (e.g., at or near the anus or the vaginal opening) to a second location above the urethral opening (e.g., at or near the clitoris or the mons pubis). The opening 106 can exhibit an elongated shape since the space between the legs of a female is relatively small when the legs of the female of closed thereby only permitting the flow of the fluid(s) along a path that corresponds to the elongated shape of the opening 106. The longitudinal axis or dimension of the fluid collection device refers to the axis or dimension that is parallel to largest dimension of the device, such as axially along a cylindrical device as show in FIG. 2A. The opening 106 in the fluid impermeable barrier 102 can exhibit a width that is measured transverse to the longitudinal direction and may be at least about 10% of the circumference of the fluid collection member 101, such as about 25%, 30%, 40%, 50%, 60%, 75%, 85%, 100% or ranges between any combination of the foregoing, of the circumference of the fluid collection member 101. The opening 106 can exhibit a width that is greater than 50% of the circumference of the fluid collection member 101 since the vacuum (e.g., suction) through the conduit 108 pulls the fluid into the conduit 108. In some embodiments, the opening 106 may be vertically oriented (e.g., having a major axis parallel to the longitudinal axis of the device 100). In some embodiments, (not shown), the opening 106 may be horizontally oriented (e.g., having a major axis perpendicular to the longitudinal axis of the device 100). In an example, one or more portions of the fluid impermeable barrier 102 can be configured to be attached to the individual, such as adhesively attached (e.g., with a hydrogel adhesive) to the individual. According to an embodiment, a suitable adhesive for the impermeable barrier (or flanges) is a hydrogel layer, such as those disclosed in U.S. Patent Application Publication No. 2017/0189225, the disclosure of which is incorporated herein by reference in its entirety.

The fluid collection member 101 includes the wicking material 115 disposed in the chamber 104. The wicking material 115 may include one or more of the fluid permeable membrane 118 and the fluid permeable support 120, each disposed in the chamber 104. The fluid permeable membrane 118 can cover at least a portion (e.g., all) of the opening 106. The fluid permeable membrane 118 can be configured to wick any fluid away from the opening 106 thereby preventing the fluid from escaping the chamber 104. The fluid permeable membrane 118 can also wick the fluid generally towards an interior of the chamber 104, as discussed in more detail below. The fluid permeable membrane 118 can include any material that can wick the fluid. For example, the fluid permeable membrane 118 can include fabric, such as a gauze (e.g., a silk, linen, polymer based materials such as polyester, or cotton gauze), another soft fabric, or another smooth fabric. Forming the fluid permeable membrane 118 from gauze, soft fabric, and/or smooth fabric can reduce chafing caused by the fluid collection member 101.

The fluid permeable support 120 may be disposed in the chamber 104, such as concentrically within the fluid permeable membrane 118. The fluid permeable support 120 may be formed from material that is more rigid (e.g., less deformable) than the fluid permeable membrane 118, such as any of the materials disposed herein for a fluid permeable membrane. For example, the fluid permeable support 120 can include a porous nylon structure. The fluid permeable support 120 is configured to support the fluid permeable membrane 118 since the fluid permeable membrane 118 can be formed from a foldable, flimsy, or otherwise easily deformable material. For example, the fluid permeable support 120 can be positioned such that the fluid permeable membrane 118 is disposed between the fluid permeable support 120 and the fluid impermeable barrier 102. As such, the fluid permeable support 120 can support and maintain the position of the fluid permeable membrane 118. In an embodiment, the fluid permeable support 120 can be omitted from the fluid collection member 101.

In an embodiment, the fluid permeable membrane 118 and the fluid permeable support 120 can at least substantially completely fill the portions of the chamber 104 that are not occupied by the conduit 108. In another example, the fluid permeable membrane 118 and the fluid permeable support 120 may not substantially completely fill the portions of the chamber 104 that are not occupied by the conduit 108. In such an example, the fluid collection device 100 includes the reservoir 122 disposed in the chamber 104. The reservoir 122 is a substantially unoccupied portion of the chamber 104. The fluid(s) that is in the chamber 104 can flow through the fluid permeable membrane 118 and/or fluid permeable support 120 to the reservoir 122. The reservoir 122 can store at least some of the fluid(s) therein.

The fluid impermeable barrier 102 can store fluid(s) in the reservoir 122. The reservoir 122 may be disposed in any portion of the interior region of the chamber 104. For example, the fluid reservoir 122 may be positioned in the second end region of the chamber 104.

In an example, the reservoir 122 can be located at the portion of the chamber 104 that is closest to the inlet 110 (e.g., the second end region). However, the reservoir 122 can be located at different locations in the chamber 104. For example, the reservoir 122 can be located at the end of the chamber 104 that is closest to the outlet 112. In another example, fluid collection device 100 can include multiple reservoirs, such as a first reservoir that is located at the portion of the chamber of the chamber 104 that is closest to the inlet 110 (e.g., second end region) and a second reservoir that is located at the portion of the of the chamber 104 that is closest to the outlet 112 (e.g., first end region). In another example, the fluid permeable support 120 is spaced from at least a portion of the conduit 108 and the reservoir 122 can be the space between the fluid permeable support 120 and the conduit 108.

Other examples of fluid impermeable barriers, fluid permeable membranes, fluid permeable supports, chambers, and their shapes and configurations are disclosed in U.S. patent application Ser. No. 15/611,587 filed on Jun. 1, 2017 and U.S. patent application Ser. No. 15/260,103 filed on Sep. 8, 2016 (published as US 2016-0374848 on Dec. 29, 2016), the disclosure of each of which is incorporated herein, in its entirety, by this reference.

The fluid impermeable barrier 102, the fluid permeable membrane 118 and the fluid permeable support 120 can be configured to have the conduit 108 at least partially disposed in the chamber 104. For example, at least one of the fluid permeable membrane 118 and the fluid permeable support 120 can be configured to form a space that accommodates the conduit 108. In another example, the fluid impermeable barrier 102 can define an aperture 124 sized to receive the conduit 108 (e.g., at least one tube). The at least one conduit 108 can be disposed in the chamber 104 via the aperture 124 in the first end region of the device 100. The aperture 124 can be configured to form an at least substantially fluid tight seal against the conduit 108 or the at least one tube thereby substantially preventing the fluid(s) from escaping the chamber 104. In some embodiments, the aperture 124 may be disposed on the second end region nearer the reservoir 122. In such embodiments, the conduit 108 may be disposed in only the second end region with the inlet 110 being disposed in the second end region (e.g., the reservoir 122).

As previously discussed, the conduit 108 is configured to be coupled to, and at least partially extend between, one or more of the fluid storage container (not shown) and the vacuum source (not shown). In an example, the conduit 108 is configured to be directly connected to the vacuum source (not shown). In such an example, the conduit 108 can extend from the fluid impermeable barrier 102 by at least one foot, at least two feet, at least three feet, or at least six feet. In another example, the conduit 108 is configured to be indirectly connected to at least one of the fluid storage container (not shown) and the vacuum source (not shown). In some embodiments, the conduit is secured to a wearer's skin with a catheter securement device, such as a STATLOCK® catheter securement device available from C. R. Bard, Inc., including but not limited to those disclosed in U.S. Pat. Nos. 6,117,163; 6,123,398; and 8,211,063, the disclosures of which are all incorporated herein by reference in their entirety.

The inlet 110 and the outlet 112 are sized, positioned, or otherwise configured to place (e.g., directly or indirectly) the vacuum source (not shown) in fluid communication with the chamber 104 (e.g., the reservoir 122). In an example, the inlet 110 and/or the outlet 112 can form a male connector. In another example, the inlet 110 and/or the outlet 112 can form a female connector. In an example, the inlet 110 and/or the outlet 112 can include ribs that are configured to facilitate secure couplings. In an example, the inlet 110 and/or the outlet 112 can form a tapered shape. In an example, the inlet 110 and/or the outlet 112 can include a rigid or flexible material.

Locating the inlet 110 at or near a gravimetrically low point of the chamber 104 enables the conduit to receive more of the fluid(s) than if inlet 110 was located elsewhere and reduce the likelihood of pooling (e.g., pooling of the fluid(s) can cause microbe growth and foul odors). For instance, the fluid(s) in the fluid permeable membrane 118 and the fluid permeable support 120 can flow in any direction due to capillary forces. However, the fluid(s) may exhibit a preference to flow in the direction of gravity, especially when at least a portion of the fluid permeable membrane 118 and/or the fluid permeable support 120 is saturated with the fluid(s).

As the vacuum source (FIG. 1) applies a vacuum/suction in the conduit 108, the fluid(s) in the chamber 104 (e.g., at the second end region such as in the reservoir 122) may be drawn into the inlet 110 and out of the fluid collection member 101 of the fluid collection device 100 via the conduit 108.

In an example, the conduit 108 is configured to be at least insertable into the chamber 104. In such an example, the conduit 108 can include one or more markers (not shown) on an exterior thereof that are configure to facilitate insertion of the conduit 108 into the chamber 104. For example, the conduit 108 can include one or more markings thereon that are configured to prevent over or under insertion of the conduit 108, such as when the conduit 108 defines an inlet 110 configured to be disposed in or adjacent to the reservoir 122. In another example, the conduit 108 can include one or more markings thereon that are configured to facilitate correct rotation of the conduit 108 relative to the chamber 104. In an example, the one or more markings can include a line, a dot, a sticker, or any other suitable marking. In some examples, the conduit may be frosted or opaque (e.g., black) to obscure visibility of the fluid(s) therein.

In an example, one or more components of the fluid collection device 100 can include an antimicrobial material, such as an antibacterial material where the fluid collection device may contact the wearer or the bodily fluid of the wearer. The antimicrobial material can include an antimicrobial coating, such as a nitrofurazone or silver coating. The antimicrobial material can inhibit microbial growth, such as microbial growth due to pooling or stagnation of the fluid(s). In an example, one or more components (e.g., impermeable barrier 102, conduit 108, etc.) of the fluid collection device 100 can include an odor blocking or absorbing material such as a cyclodextrine containing material or a thermoplastic elastomer (TPE) polymer.

The at least one flange 140 can be disposed on a lower portion of the fluid collection member 101 (e.g., substantially opposite the opening 106). For example, the at least one flange 140 may extend from the fluid collection member 101 may have the at least one flange 140 affixed to or integrally formed in the fluid impermeable barrier 102.

Figure 4:
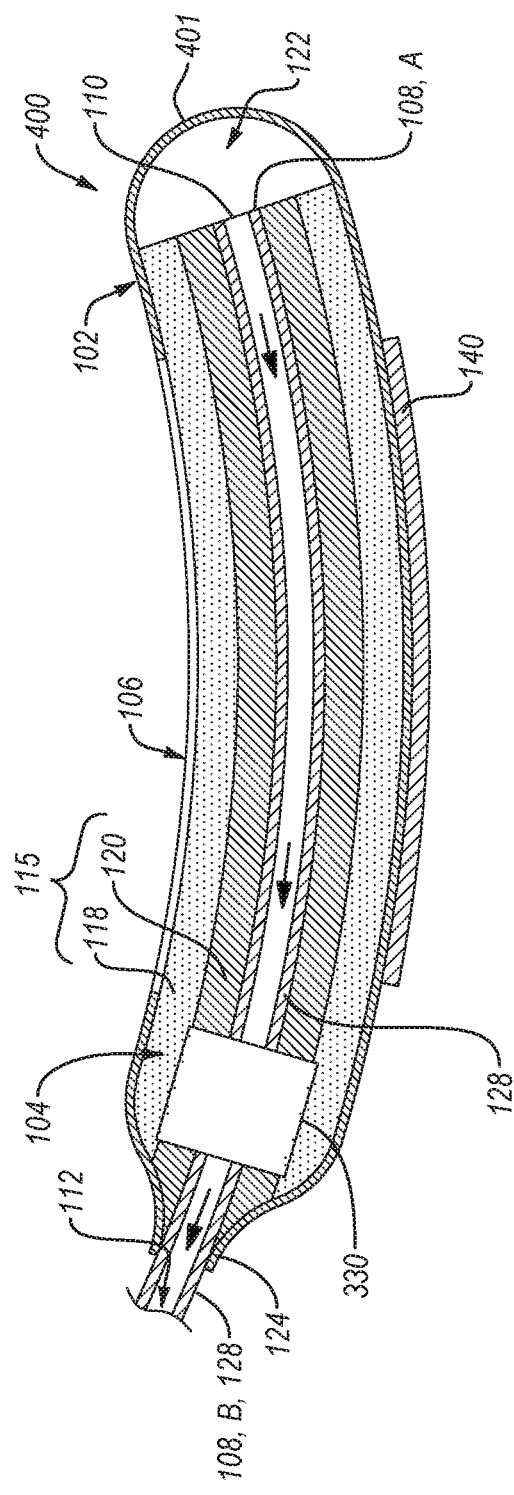

FIG. 4 is a schematic cross-sectional view of the fluid collection device 400 taken along the plane A-A of FIG. 2A, according to an embodiment. The fluid collection device 400 may include the portable vacuum source 330 disposed therein. Except as otherwise disclosed herein, the fluid collection device 400 can be the same as or substantially similar to the fluid collection device 100 of FIG. 2A, in one or more aspects. The fluid collection device 400 can include fluid collection member 401 and the at least one flange 140. The fluid collection member 401 may be similar or identical to the fluid collection member 101 in one or more aspects, such as including one or more of the fluid impermeable barrier 102 that defines the chamber 104 and the opening 106, the wicking material 115, the fluid permeable membrane 118, the fluid permeable support 120, and the reservoir 122, or the conduit 108. The fluid collection device 400 includes the portable vacuum source 330 disposed therein. The portable vacuum source 330 may be similar or identical to the vacuum source 16 as disclosed herein, in one or more aspects. The portable vacuum source 330 may be sized to fit on or within the fluid collection device. The portable vacuum source may be sized and shaped for a person to carry. As shown, the portable vacuum source 330 may be at least partially disposed within the fluid impermeable barrier 102. While a portable vacuum source 330 is depicted in FIG. 4, a fixed vacuum source (e.g., vacuum line) may alternatively or additional be used with the fluid collection device 400.

The fluid collection device 400 includes the conduit 108 that is at least partially disposed in the chamber 104. For example, the wicking material 115 (e.g., the fluid permeable membrane 118, the fluid permeable support 120) may fill a portion of the chamber 104 and leave a portion vacant thereby forming the reservoir 122 between the wicking material 115 and the fluid impermeable barrier 102. The conduit 108 can include one or more walls that define an inlet 110 and the outlet 112. The inlet 110 enables at least some of the fluid(s) that is present in the chamber 104 to enter the conduit 108. In an example, the conduit 108 can be configured to have the inlet 110 located at, near, or spaced at a gravimetrically low point of the chamber 104. In an example, the conduit 108 can be configured to have the at least one inlet 110 disposed in or adjacent to the reservoir 122. As shown the conduit 108 can extend through at least a portion of the chamber 104, such as longitudinally through at least a portion of the wicking material 115 in a concentrically central region fluid collection member 115.

The conduit 108 can be in fluid communication with the interior region (e.g., reservoir 122) of the chamber 104 via the fluid impermeable barrier 102. As such, the fluid impermeable barrier 102 can define the aperture 124. In an example, as illustrated, the aperture 124 enables the conduit 108 to extend outwardly from the chamber 104 when the conduit 108 is only partially disposed in the chamber 104. In examples, the conduit 108 may include a plurality of separate sections. For example and as shown, the conduit 108 may include a first section A and section B. The first section A may include the inlet 110 extending from the distal end (e.g., first end region) to the portable vacuum source 330 and the B section may extend from the portable vacuum source 330 out of the aperture 124, such as to a fluid storage container (not shown).

The portable vacuum source 330 may include any of the portable vacuum pumps disclosed herein. For example, the portable vacuum source 330 may include a manual vacuum pump, a diaphragm pump, a centrifugal pump, a displacement pump, a magnetically driven pump, a peristaltic pump, or any pump configured to produce a vacuum. The portable vacuum source 330 may be sized to fit in the chamber 104 inside of the fluid impermeable barrier 102. In examples, the portable vacuum source 330 may sealed in a fluid tight housing or container. The portable vacuum source 330 may apply a vacuum (e.g., suction) in the A section of the conduit 108 effective to suction fluid from the chamber 104. The fluid may travel through the A section to the B section (e.g., through the portable vacuum source 330) and out of the fluid collection device 300 via the B section by flow induced by the vacuum or suction applied by the portable vacuum source 330. For example, the portable vacuum source 330 may include a centrifugal pump and an impeller therein may draw the fluid from the chamber 104 via the inlet 110 and force the fluid out of the chamber 104 via the B section of the conduit 108. Each of the A section and the B section of the conduit 108 may be in fluid communication with (e.g., sealed) the portable vacuum source 330. In some examples, the portable vacuum source 330 and the conduit 108 can be integrally formed together (e.g., exhibit single piece construction).

Figure 5:
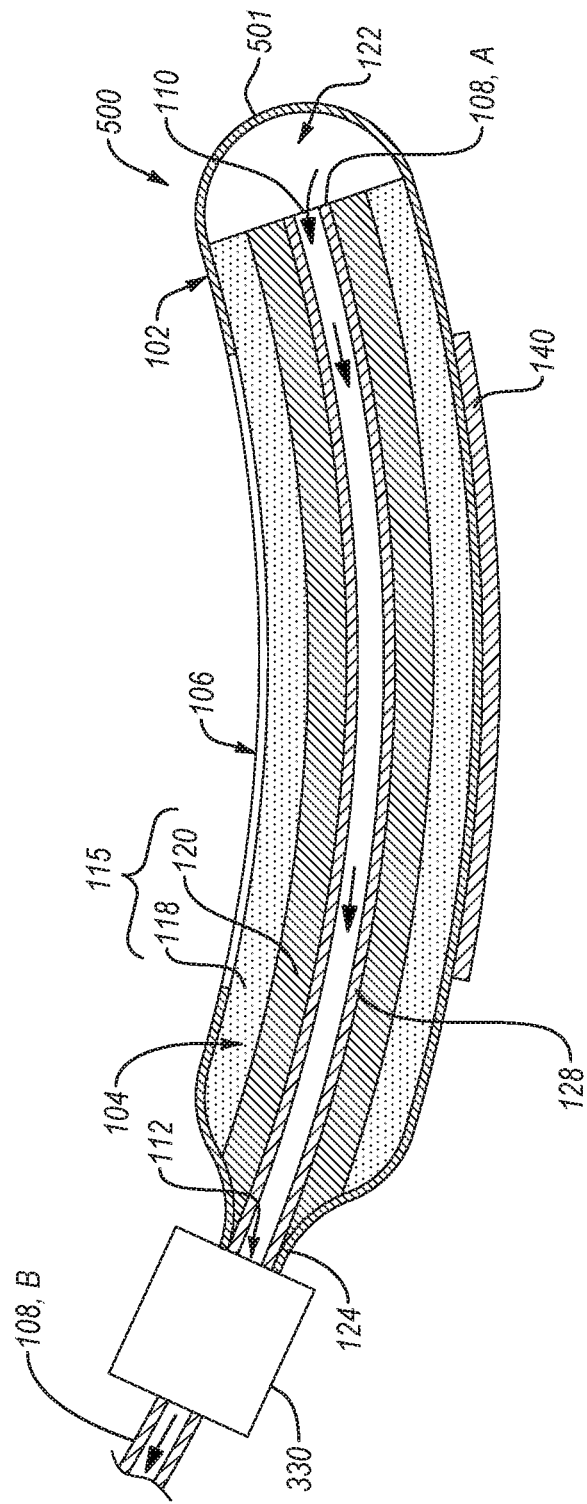

FIG. 5 is a schematic cross-sectional view of the fluid collection device 500 taken along the plane A-A of FIG. 2A, according to an embodiment. The fluid collection device 500 may include the portable vacuum source 330 disposed thereon. Except as otherwise disclosed herein, the fluid collection device 500 can be the same as or substantially similar to the fluid collection device 100 of FIG. 2A, in one or more aspects. The fluid collection device 500 can include fluid collection member 501 and the at least one flange 140. The fluid collection member 501 may be similar or identical to the fluid collection member 101 in one or more aspects, such as including one or more of the fluid impermeable barrier 102 that defines the chamber 104 and the opening 106, the wicking material 115, the fluid permeable membrane 118, the fluid permeable support 120, and the reservoir 122, or the conduit 108. The fluid collection member 501 of the fluid collection device 500 includes the portable vacuum source 330 disposed thereon. The portable vacuum source 330 may be attached to the fluid collection device 500 at or on the fluid impermeable barrier 102. While a portable vacuum source 330 is depicted in FIG. 5, a fixed vacuum source (e.g., vacuum line) may alternatively or additional be used with the fluid collection device 500.

The fluid collection device 500 includes the conduit 108 that is at least partially disposed within the fluid collection member 501. For example, the wicking material 115 (e.g., the fluid permeable membrane 118, the fluid permeable support 120) may fill a portion of the chamber 104 and leave a portion vacant thereby forming the reservoir 122 between the wicking material 115 and the fluid impermeable barrier 102. As shown the conduit 108 can extend through at least a portion of the chamber 104, such as longitudinally through at least a portion of the wicking material 115 in a concentrically central region fluid collection member 115 to the reservoir 122. The conduit 108 may extend through the wicking material 115 to the reservoir 122. The conduit 108 can include one or more walls that define an inlet 110 and the outlet 112. The inlet 110 enables at least some of the fluid(s) that is present in the chamber 104 to enter the conduit 108. In an example, the conduit 108 can be configured to have the inlet 110 located at, near, or spaced at a gravimetrically low point of the chamber 104. In an example, the conduit 108 can be configured to have the at least one inlet 110 disposed in or adjacent to the reservoir 122.

The conduit 108 can be in fluid communication with the interior region of the chamber 104 via the fluid impermeable barrier 102. As such, the fluid impermeable barrier 102 can define the aperture 124. In an example, as illustrated, the aperture 124 enables the conduit 108 to extend outwardly from the chamber 104 when the conduit 108 is only partially disposed in the chamber 104. In examples, the conduit 108 may include a plurality of separate sections. For example and as shown, the conduit 108 may include the first section A and the second section B. The first section A may include the inlet 110 extending from the distal end (e.g., first end region), out of the aperture 124, to the portable vacuum source 330 mounted thereto. The portable vacuum source 330 may be mounted to the outer surface of the fluid collection device 400. The B section may be attached to and extend from the portable vacuum source 330, such as to a fluid storage container (not shown).

The portable vacuum source 330 may include any of the portable vacuum pumps disclosed herein such as a manual vacuum pump, a diaphragm pump, a centrifugal pump, a displacement pump, a magnetically driven pump, a peristaltic pump, or any pump configured to produce a vacuum. The portable vacuum source 330 may be sized to fit in the chamber 104 inside of the fluid impermeable barrier 102. In examples, the portable vacuum source 330 may sealed in a fluid tight housing or container. The portable vacuum source 330 may apply a vacuum (e.g., suction) in the A section of the conduit 108 effective to suction fluid from the chamber 104. The fluid may travel through the A section out of the fluid collection device 400 to the portable vacuum source 330. The fluid may be removed from the portable vacuum source 330 via the B section by flow induced by the vacuum or suction applied by the portable vacuum source 330. For example, the portable vacuum source 330 may include a centrifugal pump and an impeller therein may draw the fluid from the chamber 104 via the inlet 110 and suction the fluid out of the chamber 104 via the portable vacuum source 330 to the B section of the conduit 108. Each of the A section and the B section of the conduit 108 may be in fluid communication with (e.g., sealed) the portable vacuum source 330. In some examples, the portable vacuum source 330 and the conduit 108 (e.g., one or both of the A section or the B section) can be integrally formed together to exhibit single piece construction.

The fluid collection devices shown in FIGS. 2-5 are examples of female fluid collection devices that are configured to collect fluid(s) from females (e.g., collect urine from a female urethra). However, the devices, systems, and methods disclosed herein can include male fluid collection devices shaped, sized, and otherwise configured to collect fluid(s) from males (e.g., a cup shaped fluid collection member to collect urine from a male urethra). In such examples, the flanges of the male fluid collection device may be located on the male fluid collection device to position and maintain the fluid collection device over the male urethra (e.g., penis). In any of the embodiments disclosed herein the conduits 108 may include or be operably coupled to a flow meter (not shown) to measure the flow of fluid(s) therein, one or more securement devices (e.g., a STATLOCK® securement device, not shown) or fittings to secure the conduit 108 to one or more components of the systems or devices disclosed herein (e.g., vacuum source or fluid storage container), or one or more valves to control the flow of fluid(s) in the systems and devices herein.

In an example, at least one of portion of the conduit 108 of the fluid collection devices or systems herein can be formed of an at least partially opaque material which can obscure the fluid(s) that is present therein. For example, the B section of the conduits 108 disclosed herein may be formed of an opaque material or translucent material while the A section may be formed of a transparent material or translucent material. In examples, the B section may include transparent or translucent material. Unlike the opaque or nearly opaque material, the translucent material allows a user of the devices and systems herein to visually identify fluid(s) or issues that are inhibiting the flow of fluid(s) within the conduit 108.

In any of the example, systems or devices disclosed herein, the system of fluid collection device may include moisture sensors (not shown) disposed inside of the chamber of the fluid collection device. In such examples, the moisture sensor may be operably coupled to a controller or directly to the vacuum source, and may provide electrical signals indicating that moisture is or is not detected in one or more portions of the chamber. The moisture sensor(s) may provide an indication that moisture is present, and responsive thereto, the controller of the vacuum source (e.g., vacuum device with a programmable controller) may direct the initiation of suction to the chamber to remove the fluid therefrom. Suitable moisture sensors may include capacitance sensors, volumetric sensors, potential sensors, resistance sensors, frequency domain reflectometry sensors, time domain reflectometry sensors, or any other suitable moisture sensor. In practice, the moisture sensors may detect moisture in the chamber and may provide a signal to the controller of the vacuum source to activate the vacuum source.

Figure 6:
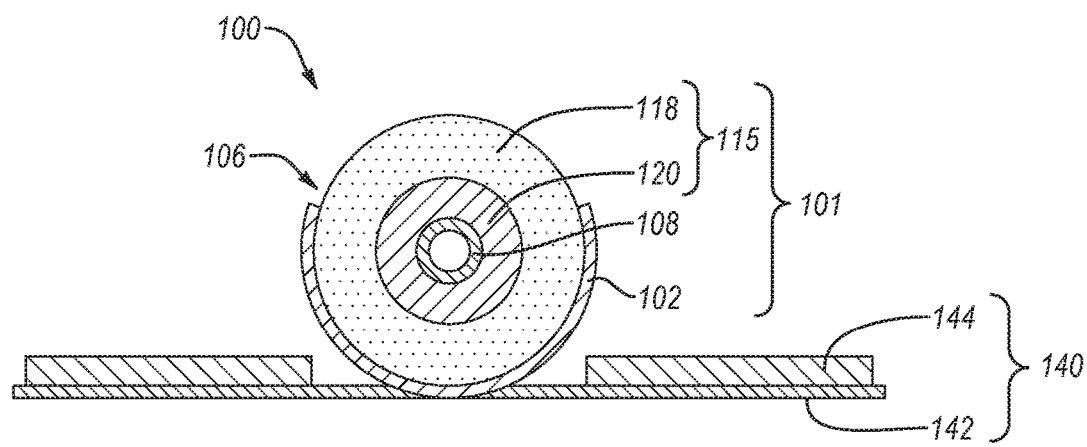
FIGS. 6-8 are schematic cross-sectional views of fluid collection devices taken along the plane B-B of FIG. 2A, according to embodiments.
Figure 7:
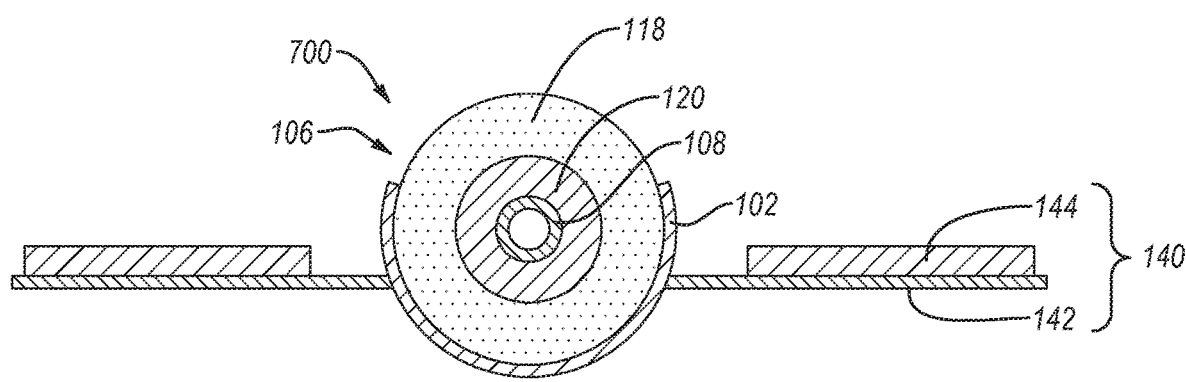
Figure 8:
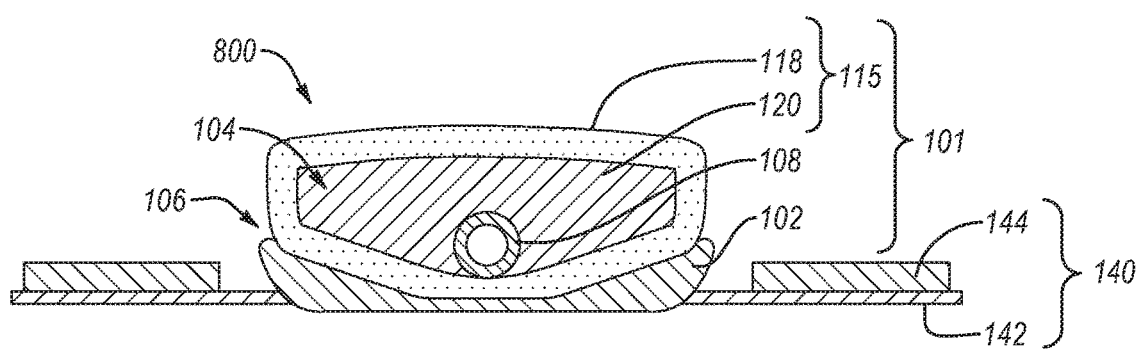

As noted above, the at least one flange 140 (e.g., pair of flanges) may be positioned on the fluid collection member in any of a number of positions and may extend therefrom at any angle. The cross-sectional shape of the fluid collection members disclosed herein may include any of various shapes or sizes. For example, the cross-sectional shape (along the plane B-B of FIG. 2A) may be substantially round (e.g., circular), elliptical, rectangular, triangular, irregular (e.g., having no specific shape), etc. FIGS. 6-8 are schematic cross-sectional views of female fluid collection devices taken along the plane B-B of FIG. 2, according to different embodiments.

FIG. 6 is a schematic cross-sectional view of the fluid collection device 100 taken along the plane B-B of FIG. 2A, according to an embodiment. The fluid collection device 100 includes the fluid collection member 101 and the at least one flange 140 extending therefrom. As shown, the fluid collection member 101 includes the fluid impermeable barrier 102, the wicking member 115 (e.g., the fluid permeable membrane 118 and the fluid permeable support 120), and the conduit 108, all concentrically arranged. As shown, the cross-sectional shape of the fluid collection member 101, and one or more components therein, may be generally round (e.g., circular or ellipsoid).

The at least one flange 140 may extend substantially tangentially from the fluid collection member 101 (e.g., the fluid impermeable barrier 102). For example, the at least one flange 140 may include at least 2 flanges 140, each extending from the fluid collection member 101 tangentially in substantially opposite directions from one another. "Substantially tangentially" may include flanges 140 that extend outwardly at an angle within 10% of 0° from an attachment point of the flange(s) on the outer surface of the fluid impermeable barrier. In examples, the at least one flange 140 may attach to the fluid collection member 101 at a point substantially opposite the opening 106. The fluid collection member 101 may extend toward the user past the flanges 140. Such arrangements may allow the fluid collection member 101 to be positioned on the region of the female urethra, such as on or between the labia.

In examples, the flange bodies 142 may have the adhesive member 144 bound thereto on a surface thereof that generally faces the same direction as the opening 106. In some examples, the flanges 140 may alternatively or additionally include adhesive members 144 on the surface of the flange body 142 that face generally away from the opening 106. The adhesive members 144 may allow the flange body 142 to be attached (e.g., temporarily adhered) to one or more skin surfaces of the subject that are adjacent to the urethra of the user, such as the thighs or pubic region. The adhesive members 144 may secure and maintain the fluid collection device 100 in a position to collect fluid from the user, such as between the labia to collect urine from a female subject.

FIG. 7 is a schematic cross-sectional view of the fluid collection device 700 taken from a view along the plane B-B of FIG. 2A, according to an embodiment. The fluid collection device 100 includes the fluid collection member 101 and the at least one flange 140 extending therefrom. As shown, the fluid collection member 101 includes the fluid impermeable barrier 102, the wicking member 115 (e.g., the fluid permeable membrane 118 and the fluid permeable support 120), and the conduit 108, all concentrically arranged. As shown, the cross-sectional shape of the fluid collection member 101, and one or more components therein, may be generally round (e.g., circular or ellipsoid).

The at least one flange 140 may extend substantially perpendicularly away from the fluid collection member 101 (e.g., the fluid impermeable barrier 102). For example, the at least one flange 140 may include at least 2 flanges 140, each extending from the fluid collection member 101 perpendicularly (e.g., in a radial direction) from the fluid impermeable barrier 102 and in substantially opposite directions from one another. "Substantially perpendicularly" may include flanges 140 that extend outwardly at an angle within 10% of 90° with respect to an outer surface of the fluid impermeable barrier at attachment point of the flange(s) 140 thereon. For examples and as shown, the at least one flange 140 may attach to the fluid collection member 101 and radially extend therefrom in radially opposite directions. The fluid collection member 101 may extend toward the user past the flanges 140. Such arrangements may allow the fluid collection member 101 to be positioned on the region of the female urethra, such as on or between the labia.

In examples, the flange bodies 142 may have the adhesive member 144 bound thereto on a surface thereof that generally faces the same direction as the opening 106. In some examples, the flanges 140 may alternatively or additionally include adhesive members 144 on the surface of the flange body 142 that face generally away from the opening 106. The adhesive members 144 may allow the flange body 142 to be attached (e.g., temporarily adhered) to one or more skin surfaces of the subject that are adjacent to the urethra of the user, such as the thighs or pubic region. The adhesive members 144 may secure and maintain the fluid collection device 100 in a position to collect fluid from the user, such as between the labia to collect urine from a female subject.

The cross-sectional shape of the fluid collection member and the position(s) of the components therein may vary. FIG. 8 is a schematic cross-sectional view of the fluid collection device 800 taken from a view along the plane B-B of FIG. 2A, according to an embodiment. The fluid collection device 800 may be similar or identical to the fluid collection device 100, in one or more aspects. The fluid collection device 800 includes the fluid collection member 801 and the at least one flange 140 extending therefrom. The fluid collection member 801 may be similar or identical to the fluid collection member 101, in one or more aspects. For example, the fluid collection member 801 includes the fluid impermeable barrier 102, the wicking member 115 (e.g., the fluid permeable membrane 118 and the fluid permeable support 120), and the conduit 108. The cross-sectional shape of the fluid collection member 801 may be generally rectangular (e.g., with rounded corners) as shown, or elliptical. In such examples, the fluid collection member 801 may provide coverage (e.g., fluid absorption) of a larger surface area than the fluid collection member 101 (FIG. 6). In examples, the fluid impermeable barrier 102 may be shaped to provide a relatively wide cross-sectional shape. As shown, the fluid impermeable barrier 102 may form the chamber 104 having a gravimetrically low portion, such as in a V-notched or dished shape. The wicking material 115 may fill at least a portion of the chamber 104. For example, the fluid permeable support 120 may fill an interior portion of the chamber 104, and the fluid permeable member 118 may extend around at least a portion of the fluid permeable support 120. In examples, the fluid permeable support 120 may include region therein for accommodating the conduit 108. In examples, the conduit 108 may be disposed in the gravimetrically low point or region of the chamber 104. As shown, one or more of the conduit 108, fluid permeable member 118, or the fluid permeable support 120 may be non-concentrically disposed (e.g., not centered) in the fluid collection member 801 or fluid impermeable barrier 102.

Additional or alternative shapes for the fluid collection members are considered. For example, the fluid collection member may have a substantially triangular cross-sectional shape where a corner or apex of the triangle faces the user.

The at least one flange 140 may extend substantially perpendicularly away from the fluid collection member 801 (e.g., the fluid impermeable barrier 102). For example, the at least one flange 140 may include at least 2 flanges 140, each extending from the fluid collection member 801 perpendicularly from the fluid impermeable barrier 102 and in substantially opposite directions from one another. For examples and as shown, the at least one flange 140 may attach to the fluid collection member 801 in radially opposite directions. The fluid collection member 801 may extend toward the user past the flanges 140. Such arrangements may allow the fluid collection member 801 to be positioned on the region of the female urethra, such as on or between the labia.

In examples, the flange bodies 142 may have the adhesive member 144 bound thereto on a surface thereof that generally faces the same direction as the opening 106. In some examples, the flanges 140 may alternatively or additionally include adhesive members 144 on the surface of the flange body 142 that face generally away from the opening 106. The adhesive members 144 may allow the flange body 142 to be attached (e.g., temporarily adhered) to one or more skin surfaces of the subject that are adjacent to the urethra of the user, such as the thighs or pubic region. The adhesive members 144 may secure and maintain the fluid collection device 100 in a position to collect fluid from the user, such as between the labia to collect urine from a female subject.

In some examples, the fluid collection devices herein may include more than one conduit therein. the more than one conduit may be disposed in a plurality of regions therein. In examples, conduit 108 may include a plurality of inlets.

Figure 9A:
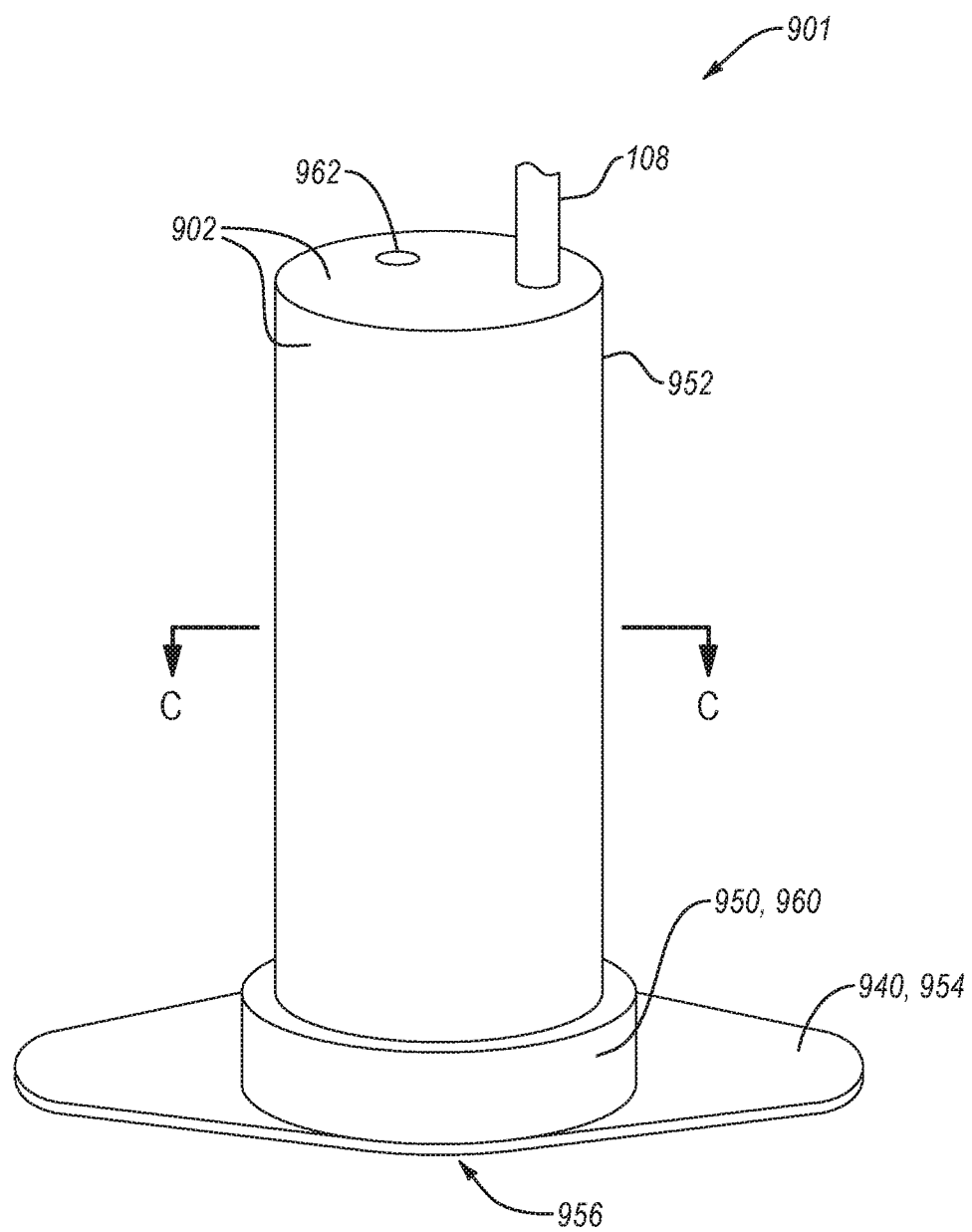
FIG. 9A is an isometric view of a fluid collection device, according to an embodiment.
Figure 9B:
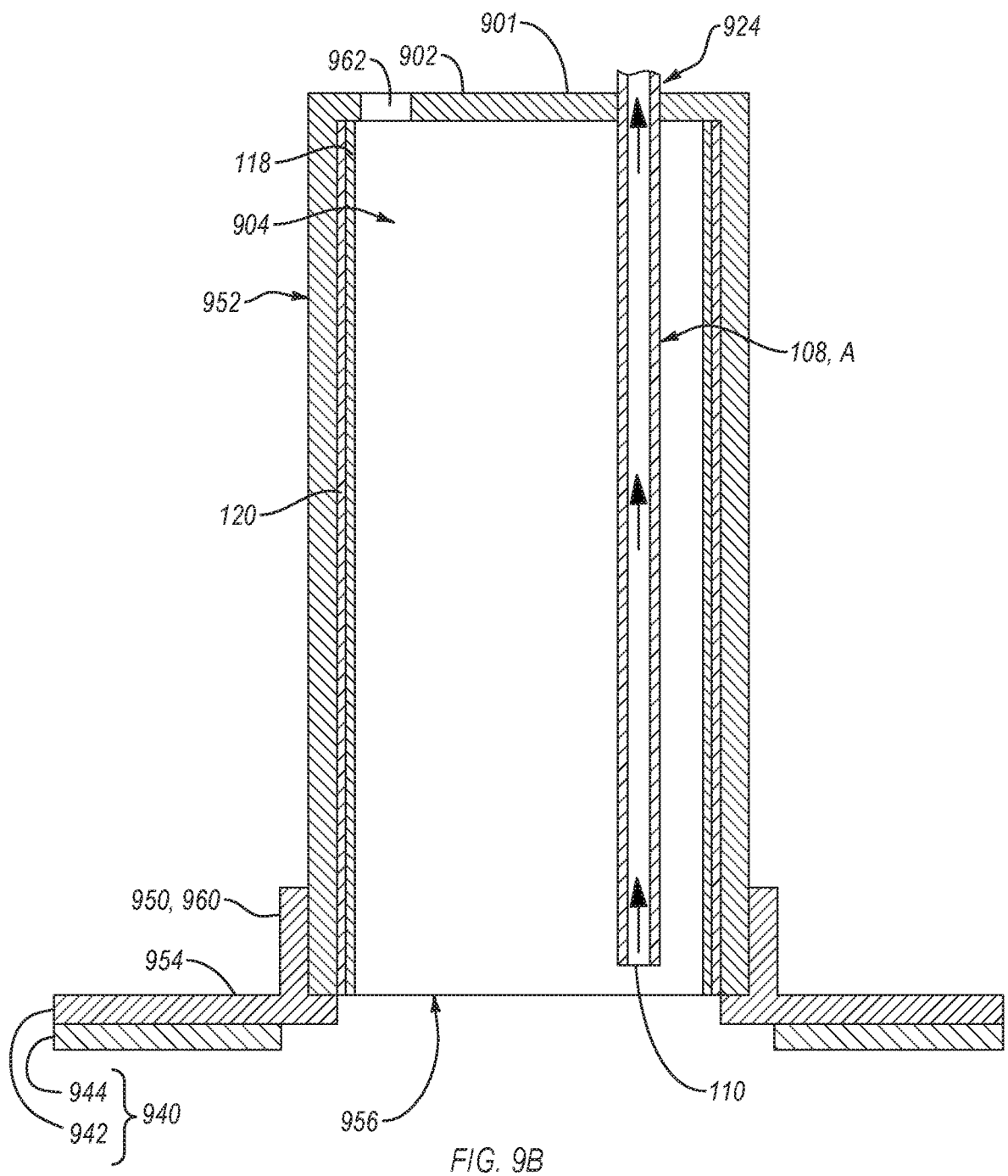
FIG. 9B is schematic cross-sectional view of the fluid collection device taken along the plane C-C of FIG. 9A, according to an embodiment.

Fluid collection devices having flanges thereon may be configured for use with male users. Devices and methods described herein can be configured to collect urine from a male user, such as having a fluid collection device shaped and sized to receive a male urethra (e.g., penis) therein. FIGS. 9A and 9B are isometric and schematic cross-sectional views of a male fluid collection device 900, according to an embodiment.

Referring to FIGS. 9A and 9B, the fluid collection device 900 includes a receptacle 950 and a cup portion 952. The receptacle 950 is sized, shaped, and made of a material to be coupled to skin that surrounds the male urethra and have the male urethra positioned therethrough. For example, the receptacle 950 can include an annular base 954 that defines an opening 956 in the receptacle 950. The annular base 954 is sized and shaped to be positioned around the male urethra (e.g., positioned around and/or over the penis) and the opening 956 can be configured to have the male urethra positioned therethrough. The annular base 954 can also be sized, shaped, made of a material, or otherwise configured to be coupled (e.g., adhesively attached, such as with a hydrogel adhesive) to the skin around the male urethra (e.g., around the penis) with one or more flanges 940. In examples, the receptacle 950 may include one or more flanges that extend outwardly to contact the wearer of the fluid collection device 900. The annular base 954 may include, define, or be affixed to at least one flange 940 that extends substantially perpendicular to the lip 960.

The flange(s) 940 may be similar or identical to the flange 140 disclosed herein, in one or more aspects. For example, the flange 940 may include the flange body 942 and an adhesive 944 (or other attachment body for attaching the flange body 942 to a subject or clothes of the subject). The flange body 942 may be similar or identical to the flange body 142 disclosed herein, in one or more aspects. For example, the flange body 942 may be formed from a thermoplastic elastomer, polyethylene, polyvinyl chloride, ethylene vinyl acetate, polytetrafluoroethylene, latex, silicon, fabric, woven cloth, etc. The flange body 942 may extend substantially perpendicularly to the lip 960. The adhesive 944 may be similar or identical to the adhesive 144 disclosed herein, in one or more aspects. In some examples, the more than two flanges 940 may extend from the annular base 954. In some examples (not shown), the flange 940 may include a single flange body 942 that extends from and around substantially all of the annular base 954. In such examples, the adhesive 944 may be located at discrete points or around substantially all of the surface of the flange body 942 that is expected to contact the wearer. One or more portions of the receptacle 950 may be formed from the same material as the fluid impermeable barrier 102 such as a fluid impermeable polymer (e.g., silicone, polypropylene, polyethylene, polyethylene terephthalate, polyurethane, a polycarbonate, polyvinyl chloride, latex, silicone, etc.), a metal film, another suitable material, or combinations thereof.

In an example, the annular base 954 can exhibit the general shape of the skin surface that the annular base 954 is selected to be coupled with and/or can be flexible thereby allowing the annular base 954 to conform to any shape of the skin surface. The receptacle 950 also defines a hollowed region that is configured to receive (e.g., seal against) the cup portion 952. For example, the receptacle 950 can include the lip 960 that extends upwardly from the annular base 954. The lip 960 may be tall enough to prevent the cup portion 952 from being accidentally removed from the receptacle 950 (e.g., at least 0.5 cm tall, 1 cm tall, at least 2 cm tall, or at least 5 cm tall). In some examples, the annular base 954 is optional. For example, the receptacle 950 may only include the flange 954. In some examples (not shown), the fluid collection device may have a one piece design, with the cup portion 952 and the receptacle 950 being a single piece. In some examples, the receptacle 950 is optional.

The cup portion 952 includes (e.g., may be formed from) a fluid impermeable barrier 902 that is sized and shaped to fit into the hollowed region of the receptacle 950. The cup portion 952 may be shaped to retain a fluid therein. For example, the fluid impermeable barrier 902 may define the cup portion 952, such as a substantially tubular (e.g., cylindrical) body having an enclosed end as illustrated in FIGS. 9A and 9B. Accordingly, the cup portion 552 may have a generally cupped shape with a chamber 504 therein. The fluid impermeable barrier 902 may be similar or identical to the fluid impermeable barrier 102, in one or more aspects. The fluid impermeable barrier 902 partially defines the chamber 904. The fluid impermeable barrier 902 may also define an opening 956 extending through the fluid impermeable barrier 902 that is configured to have a male urethra positioned therethrough. The fluid impermeable barrier 902 may also include at least one passageway 962 (e.g., vacuum relief hole) that allows the chamber 904 to remain substantially at atmospheric pressure. The at least one passageway 962 may be located at any point on the cup portion 952, such as near or nearer the opening 956. The cup portion 952 also includes at least a portion of the conduit 108 therein, such as at least partially disposed in the chamber 904. For example, the conduit 108 may extend from the cup portion 952 to a region at least proximate to the opening 956. The region proximate to the opening 956 may be disposed near or on the skin around the male urethra (e.g., on the penis). Accordingly, when a patient lays on their back, fluid (e.g., urine) may aggregate near the opening 956 against the skin of the subject. The fluid may be removed from the chamber 904 via the conduit 108. In some examples, the cup portion 952 of the fluid impermeable barrier 902 may be constructed of a material and/or have a thickness that allows the cup portion 952 to collapse when placed under vacuum, such as to remove air around a penis in the fluid collection device 900 during use. In such examples, the conduit 108 may extend only into the chamber 904 at the aperture 924 (e.g., not through to the area adjacent the opening). In such examples, urine may be collected and removed from the fluid collection device 900 at the end nearest the aperture 924. In such examples, the at least one passageway may be located nearest the opening 956.

The fluid collection device 900 may include wicking material therein. The fluid collection device 900 may include the fluid permeable membrane 118. The fluid permeable membrane 118 may be disposed between the fluid impermeable barrier 902 of the cup portion 952 and a penis inserted into the chamber 904. The fluid collection device 900 may include a fluid permeable support 120. The fluid permeable support 120 may be positioned between the cup portion 952 and a penis inserted into the chamber 904, such as between the fluid permeable membrane 118 and the fluid impermeable barrier 902. The sidewalls or the end of the chamber 904 may be covered with one or both the fluid permeable membrane 118 or the fluid permeable support 120.

In some examples, a vacuum source (e.g., vacuum source 16 of FIG. 1) may be remotely located from the cup portion 952. In such examples, the conduit 108 may extend out of and away from the cup portion 952 to the vacuum source (e.g., portable vacuum source). The inlet 110 of the conduit 108 is in fluid communication with the vacuum source, either directly or indirectly. The outlet (not shown) may be in fluid communication with a fluid storage container (not shown) through the conduit 108 in the direction shown by the arrows. The fluid impermeable barrier 902 may include at least one aperture 924 that is sized and shaped to receive and seal against the conduit 108, such as within the chamber 904. Accordingly, the interior region of the chamber 904 may be in fluid communication with the vacuum source 16 via the conduit 108. As the vacuum source applies a vacuum/suction in the direction of the arrows in FIG. 9B, the fluid in the chamber 904 may be removed through the conduit 108. In some examples, the fluid may be pumped via the vacuum source 16 through one or more sections of conduit to the fluid storage container (not shown). In some examples, the vacuum source may be located on or in the cup portion 952 in a manner similar or identical to the vacuum source 330 located within or on the fluid impermeable barrier 102 in FIGS. 4 and 5, in one or more aspects.

In an example, portions of the chamber 904 may be substantially empty due to the varying sizes and rigidity of the male penis. However, in some examples, the outermost regions of the chamber 904 (e.g., periphery of the interior regions of the cup portion 952) can include a porous material (e.g., one or more of the fluid permeable membrane 118 and fluid permeable support 120) positioned (e.g., at the end of the cavity) and configured to blunt a stream of urine from the male urethra, thereby limiting splashing and/or to direct the fluid(s) to a selected region of the chamber 904. Since the chamber 904 is substantially empty (e.g., substantially all of the chamber 904 forms a reservoir), the fluids are likely to pool at a gravimetrically low point of the chamber 904. The gravimetrically low point of the chamber 904 can be at an intersection of the skin of an individual and the fluid collection device 900, a corner formed in the cup portion 952, or another suitable location depending on the orientation of the wearer. The inlet 110 of the conduit 108 can be positioned to be adjacent or proximate to the gravimetrically low point of the chamber 904, such as adjacent to the annular base 954. For example, the inlet 110 may be co-extensive with or offset from the opening 956. In examples, the inlet may be positioned adjacent to the terminal end of the cup portion 952 (e.g., substantially opposite the opening).

During operation, a male using the fluid collection device 900 can discharge fluid(s) (e.g., urine) into the chamber 904. The fluid(s) can pool or otherwise be collected in the chamber 904. At least some of the fluid(s) can enter the interior of the conduit 108 via the inlet 110. The fluid may be drawn out of the fluid collection device 900 via the vacuum/suction provided by the vacuum source. In some examples, during operation, the passageway 962 may substantially maintain the pressure in the chamber 904 at atmospheric pressure even though fluid is introduced into and subsequently removed from the chamber 904.

Figure 10:
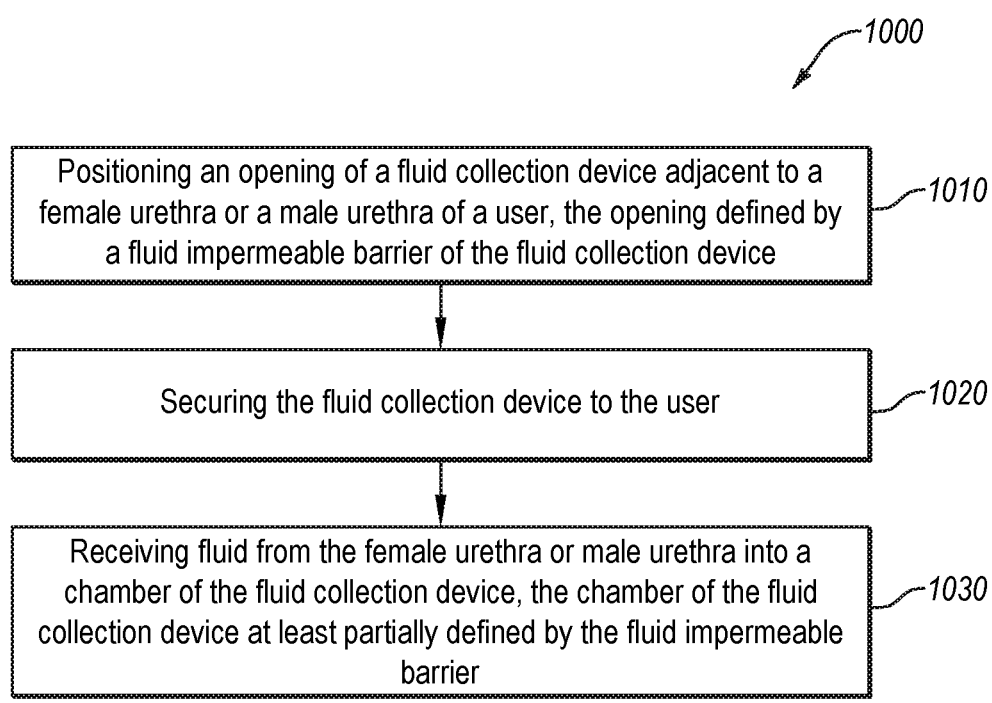
FIG. 10 is a flow diagram of a method to collect fluid, according to an embodiment.

FIG. 10 is a flow diagram of a method 1000 to use any of the fluid collection devices, members, and/or fluid collection systems disclosed herein, according to an embodiment. The method 1000 can include act 1010, which recites "positioning an opening of a fluid collection device adjacent to a female urethra or around a male urethra of a user, the opening defined by a fluid impermeable barrier of the fluid collection device." Act 1010 may be followed by act 1020, which recites "securing the fluid collection device to the user." Act 1020 may be followed by act 1030, which recites "receiving fluid from the female urethra or male urethra into a chamber of the fluid collection device, the chamber of the fluid collection device at least partially defined by the fluid impermeable barrier."

Acts 1010, 1020, 1030 of the method 1000 are for illustrative purposes. For example, the act 1010, 1020, 1030 of the method 1000 can be performed in different orders, split into multiple acts, modified, supplemented, or combined. In an example, one or more of the acts 1010, 1020, 1030 of the method 1000 can be omitted from the method 1000. Any of the acts 1010, 1020, or 1030 can include using any of the fluid collection devices or systems disclosed herein.

Act 1010 recites "positioning an opening of a fluid collection device adjacent to a female urethra or around a male urethra of a user, the opening defined by a fluid impermeable barrier of the fluid collection device." In some examples, act 1010 can include positioning the opening of a female fluid collection device such that the fluid permeable membrane of the female fluid collection device abuts or is positioned proximate to the female urethra. For example, positioning an opening of a fluid collection device adjacent to a female urethra of a user may include positioning opening of the fluid collection member of the fluid collection device on, adjacent to, between the labia. In examples the female fluid collection device may be similar or identical to the fluid collection device 100, 400, 500, 700, or 800 (FIGS. 2A-8), in one or more aspects.

In some examples, act 1010 can include positioning the opening of a male fluid collection device around a urethra of a male user such that the urethra of the user is positioned within the fluid collection device. For example, positioning an opening of a fluid collection device around a male urethra of a user may include positioning the penis of a user in the cup portion of the male fluid collection device. In examples the male fluid collection device may be similar or identical to the fluid collection device 900 (FIG. 9), in one or more aspects. In such examples, the method 1000 can include positioning a cup portion of the male fluid collection device in a hollowed region of the receptacle such that the male urethra is positioned in the cup portion through the opening in the receptacle of the male fluid collection device. The flanges on the receptacle may be used to secure the fluid collection device to a male user.

Act 1020 recites, "securing the fluid collection device to the user." Securing the fluid collection device to the user may include affixing one or more flanges of the fluid collection device to the user or clothing of the user. In examples, securing the fluid collection device to the user can include adhering the adhesion member of the at least one flange of the fluid collection device to the user. In examples, securing the fluid collection device to the user can include adhering the adhesion member(s) of the at least one flange (e.g., flanges) of the fluid collection device to one or more of the lower abdomen, inner thigh(s), testicles, pubic region, hip region, or perineum of the user (or on clothing over any of the aforementioned regions). For example, securing the fluid collection device to the user can include adhering the adhesion member(s) of the at least one flange of the fluid collection device to the inner thigh(s) of a female user. Securing the fluid collection device to the user can include adhering the adhesion member of the at least one flange of the fluid collection device to the garment (e.g., the underwear) of the user. For example, adhering the adhesion member of the at least one flange of the fluid collection device to the garment may include adhering one or more flanges on or around the crotch (e.g., gusset) of underwear of the user. Securing the fluid collection device to the user may include securing the fluid collection device to the user to maintain the opening adjacent to, on, or over the urethra of the user, even when the user moves.

Act 1030 recites "receiving fluid from the female urethra or male urethra into a chamber of the fluid collection device, the chamber of the fluid collection device at least partially defined by the fluid impermeable barrier." In examples, act 1030 can include retaining the fluid within the chamber, such as in a gravimetrically low point therein. In some examples, act 1030 can include wicking the fluid away from the opening using wicking material (e.g., fluid permeable membrane and a fluid permeable support). In some examples, act 1030 can include receiving the fluid into the chamber of the fluid collection device. In either example, act 1030 can include flowing the fluid towards a portion of the chamber that is in fluid communication with an inlet of a conduit in fluid communication with a vacuum source. For instance, act 1030 can include flowing the fluid to a substantially unoccupied portion of the chamber (e.g., a reservoir), to a gravimetrically low point of the chamber, etc. The fluid can include one or more fluids, such as urine, liquid blood, sweat, etc. In some examples, receiving fluid from the female urethra into a chamber of the fluid collection device, the chamber of the fluid collection device at least partially defined by the fluid impermeable barrier may include wicking the fluid into the chamber via the fluid permeable membrane and fluid permeable support of the fluid collection device. For example, wicking the fluid into the chamber via the fluid permeable membrane and fluid permeable support may include wicking urine into the reservoir in the fluid collection device.

The method 1000 may include removing at least some of the fluid from the fluid collection device. For example, removing at least some of the fluid from the fluid collection device may include removing the fluid from within the chamber of the fluid collection device. Such removal may include applying suction with a vacuum source effective to suction the fluid from the chamber via a conduit disposed therein (which conduit may be in fluid communication with the vacuum source). In examples, removing fluids from the fluid collection device by applying suction with a vacuum source effective to suction (e.g., vacuum) the fluid from the chamber via a conduit disposed therein include using any of the vacuum sources disclosed herein, such as a portable vacuum source. In an example, applying suction can include activating the vacuum source (e.g., portable suction device) in fluid communication with the inlet of the conduit in the fluid collection device. In examples, activating the vacuum source in fluid communication with the inlet of the conduit in the fluid collection device can include supplying power to the vacuum source by one or more of flipping an on/off switch, pressing a button, opening a valve, connecting the fluid collection device into a vacuum line, plugging a portable vacuum source into a power outlet, putting batteries into the portable vacuum source, etc. In examples, the vacuum source may include a hand operated vacuum pump and applying suction with a vacuum source may include manually operating the hand operated vacuum pump effective to suction the fluid from the chamber via the conduit disposed therein that is in fluid communication with the (portable) vacuum source. In examples, the vacuum source may include a plumbed vacuum line and applying suction with a vacuum source may include manually connecting to the plumbed vacuum line to the fluid collection device (e.g., the conduit) or opening a valve therebetween effective to suction the fluid from the chamber via the conduit disposed therein.

In examples, applying suction with a vacuum source effective to suction the fluid from the chamber via a conduit disposed therein and in fluid communication with the vacuum source can be effective to remove at least some fluid (e.g., urine) from the chamber (e.g., interior region) of the fluid collection device. In examples, applying suction with a vacuum source effective to suction the fluid from the chamber via a conduit disposed therein and in fluid communication with the vacuum source can be effective to transfer at least some of the fluid from the chamber of the fluid collection device to a fluid storage container (e.g., a bottle or bag). In some examples, applying suction with a vacuum source effective to suction the fluid(s) from the chamber may include removing fluid from one or more of a reservoir, fluid permeable support, or fluid permeable membrane of the fluid collection device.

In examples, the vacuum source (e.g., suction device) may disposed on or within the fluid collection device and applying suction with the vacuum source may include activating the vacuum source. In examples, the vacuum source may be spaced from the fluid collection device and applying suction with the vacuum source may include activating the vacuum source, such as a portable vacuum source.

In examples, applying suction with a vacuum source effective to suction the fluid from the chamber via a conduit disposed therein and in fluid communication with the vacuum source may include detecting moisture in the chamber (e.g., via one or more moisture sensors) and responsive thereto, activating the vacuum source to provide suction in the chamber. The control of the vacuum source responsive to the signals indicating that moisture or a level thereof is present in the chamber can be automatic, such as via a controller, or may merely provide an indication that a level of moisture is present that may necessitate removal of fluid from the chamber of the fluid collection device. In the latter case, a user may receive the indication and activate the vacuum source such as a pump.

In an example, the method 1000 can include collecting the fluid that is removed from the fluid collection device, such as into a fluid storage container that is spaced from the fluid collection device and in fluid communication with the conduit. The fluid storage container can include any of the fluid storage containers disclosed herein.

While various aspects and embodiments have been disclosed herein, other aspects and embodiments are contemplated. The various aspects and embodiment disclosed herein are for purposes of illustration and are not intended to be limiting.

We claim:

1. A fluid collection device, comprising:
   a fluid collection member, including:
      a fluid impermeable barrier at least partially defining a chamber, the fluid impermeable barrier also defining an opening extending therethrough, the opening configured to be positioned adjacent to a female urethra or have a male urethra positioned therethrough;
      wicking material disposed at least partially within the chamber; and
      a conduit disposed within the chamber, the conduit including an inlet positioned within the fluid collection device and an outlet configured to be fluidly coupled to a portable vacuum source; and
   at least one flange extending outwardly from the fluid collection member, the at least one flange including a flange body having an adhesive member thereon, wherein the flange body is attached to the fluid impermeable barrier.

2. The fluid collection device of claim 1, wherein the at least one flange extends substantially tangentially from the fluid collection member.

3. The fluid collection device of claim 1, wherein the at least one flange extends substantially perpendicularly from the fluid collection member.

4. The fluid collection device of claim 1, wherein the fluid collection member is substantially cylindrical.

5. The fluid collection device of claim 1, wherein the wicking material includes one or more of a fluid permeable membrane or a fluid permeable support.

6. The fluid collection device of claim 5, wherein the fluid permeable membrane extends across the opening and the fluid permeable support is disposed beneath the fluid permeable membrane.

7. The fluid collection device of claim 5, further comprising a reservoir defined between the fluid impermeable barrier and one or more of the fluid permeable membrane or the fluid permeable support, and wherein the inlet is positioned in or adjacent to the reservoir.

8. The fluid collection device of claim 1, wherein the fluid impermeable barrier is shaped to form a cup portion that connects with a receptacle configured to be positioned against a user, and the at least one flange extends from the receptacle.

9. A fluid collection system, comprising:
   a fluid storage container configured to hold a fluid;
   a fluid collection device in fluid communication with the fluid storage container, the fluid collection device including:
      a fluid collection member, including:
         a fluid impermeable barrier at least partially defining a chamber, the fluid impermeable barrier also defining an opening extending therethrough, the opening configured to be positioned adjacent to a female urethra or have a male urethra positioned therethrough;
         a wicking material disposed at least partially within the chamber; and
         a conduit disposed within wicking material, the conduit including an inlet positioned within the fluid collection device and an outlet configured to be in fluid communication with a vacuum source; and
      at least one flange extending outwardly from the fluid collection member, the at least one flange including a flange body and an adhesive member thereon, wherein the flange body is attached to the fluid impermeable barrier;
   a vacuum source in fluid communication with one or more of the fluid storage container or the fluid collection device, the vacuum source configured to draw fluid from the fluid collection device.

10. The fluid collection system of claim 9, wherein the fluid collection member includes a generally cylindrical shape.

11. The fluid collection system of claim 9, wherein the at least one flange extends substantially perpendicularly from the fluid impermeable barrier.

12. The fluid collection system of claim 9, wherein the at least one flange extends substantially tangentially from the fluid impermeable barrier.

13. The fluid collection system of claim 9, wherein the vacuum source includes a portable vacuum source disposed within the fluid collection device.

14. The fluid collection system of claim 9, wherein:
   the fluid collection device is spaced from and positioned upstream from the fluid storage container; and
   the vacuum source is positioned downstream from and outside of the fluid collection device.

15. A method to collect fluid, the method comprising:
   positioning an opening of a fluid collection device adjacent to a female urethra or a male urethra of a user, the opening defined by a fluid impermeable barrier of the fluid collection device;
   securing the fluid collection device to the user with at least one flange attached to the fluid collection device; and
   receiving fluid from the female urethra or male urethra into a chamber of the fluid collection device, the chamber of the fluid collection device at least partially defined by the fluid impermeable barrier.

16. The method of claim 15, wherein securing the fluid collection device to the user includes affixing the at least one flange to the user or clothing of the user.

17. The method of claim 15, wherein:
   the fluid collection device is configured as a female fluid collection device having:
      a fluid impermeable barrier defining a chamber therein;
      at least one flange extending from the fluid impermeable barrier, the at least one flange including a flange body and an adhesive member therein, wherein the flange body is attached to the fluid impermeable barrier; and
a conduit extending into the chamber; and
securing the fluid collection device to the user includes attaching the at least one flange to skin or clothing of the user.

18. The method of claim 15, wherein:
the fluid collection device is configured as a male fluid collection device having:
a fluid impermeable barrier defining a cup portion; and
a receptacle configured to be positioned against the user and hold the cup portion thereon, the receptacle including at least one flange extending therefrom, the at least one flange including a flange body and an adhesive member therein, wherein the flange body is attached to the fluid impermeable barrier; and
a conduit extending into the chamber; and
securing the fluid collection device to the user includes attaching the at least one flange to skin or clothing of the user.

19. The method of claim 15, further comprising removing at least some of the fluid from the fluid collection device with a vacuum source effective to suction the fluid from the chamber via a conduit disposed therein and in fluid communication with the vacuum source.

20. The method of claim 15, wherein the vacuum source is disposed within the fluid collection device and applying suction with the vacuum source includes activating the vacuum source.

21. The method of claim 15, wherein the vacuum source is spaced from the fluid collection device and applying suction with the vacuum source includes activating the vacuum source.

* * * * *